(12) United States Patent
Ibrahim et al.

(10) Patent No.: US 8,430,875 B2
(45) Date of Patent: Apr. 30, 2013

(54) MAGNETIC NAVIGATION SYSTEMS AND METHODS

(75) Inventors: Tamer Ibrahim, Pleasant Hill, CA (US); David K. Swanson, Campbell, CA (US)

(73) Assignee: ESTECH, Inc. (Endoscopic Technologies, Inc.), San Ramon, CA (US)

( * ) Notice: Subject to any disclaimer, the term of this patent is extended or adjusted under 35 U.S.C. 154(b) by 325 days.

(21) Appl. No.: 12/781,072

(22) Filed: May 17, 2010

(65) Prior Publication Data

US 2011/0060331 A1 Mar. 10, 2011

Related U.S. Application Data

(60) Provisional application No. 61/179,564, filed on May 19, 2009.

(51) Int. Cl.
*A61B 18/18* (2006.01)
(52) U.S. Cl.
USPC .......................................................... 606/41
(58) Field of Classification Search ............... 606/41, 606/45–50
See application file for complete search history.

(56) References Cited

U.S. PATENT DOCUMENTS

| | | | |
|---|---|---|---|
| 3,745,998 A | 7/1973 | Rose | |
| 4,224,929 A | 9/1980 | Furihata | |
| 4,445,892 A | 5/1984 | Hussein et al. | |
| 4,961,738 A | 10/1990 | Mackin | |
| 4,991,578 A | 2/1991 | Cohen | |
| 5,336,252 A | 8/1994 | Cohen | |
| 5,409,483 A | 4/1995 | Campbell et al. | |
| 5,423,805 A | 6/1995 | Brucker et al. | |
| 5,429,131 A * | 7/1995 | Scheinman et al. | 600/374 |
| 5,503,617 A | 4/1996 | Jako | |
| 5,593,405 A | 1/1997 | Osypka | |
| 5,672,153 A | 9/1997 | Lax et al. | |
| 5,727,569 A | 3/1998 | Benetti et al. | |
| 5,769,847 A | 6/1998 | Panescu et al. | |
| 5,782,746 A | 7/1998 | Wright | |
| 5,807,243 A | 9/1998 | Vierra et al. | |

(Continued)

OTHER PUBLICATIONS

Borst, Cornelius, et al., "Coronary artery bypass grafting without cardiopulmonary bypass and without interruption of native coronary flow using a novel anastomosis site restraining device ("Octopus")," JACC vol. 27, No. 6, May 1996, pp. 1356-1364.

(Continued)

*Primary Examiner* — Michael Peffley
(74) *Attorney, Agent, or Firm* — Kilpatrick Townsend & Stockton LLP

(57) ABSTRACT

Systems and methods for forming a lesion on an endocardial tissue of a patient's heart involve placing an ablation assembly inside of the heart and adjacent to the endocardial tissue, and placing a guiding assembly outside of the heart. An ablation assembly includes an ablation element and a first attraction element, and a guiding assembly includes a second attraction element. First and second attraction elements can be attracted via magnetism. Techniques involve forming an ablation on the cardiac tissue of a patient's heart with an ablation element of the ablation assembly. Optionally, techniques may include moving the second attraction element of the guiding assembly relative to the patient's heart, so as to effect a corresponding movement of the ablation element of the ablation assembly.

20 Claims, 19 Drawing Sheets

U.S. PATENT DOCUMENTS

| | | | |
|---|---|---|---|
| 5,820,591 A | 10/1998 | Thompson et al. | |
| 5,836,311 A | 11/1998 | Borst et al. | |
| 5,865,730 A | 2/1999 | Fox et al. | |
| 5,927,284 A | 7/1999 | Borst et al. | |
| 5,976,132 A | 11/1999 | Morris | |
| 6,013,027 A | 1/2000 | Khan et al. | |
| 6,015,378 A | 1/2000 | Borst et al. | |
| 6,036,641 A | 3/2000 | Taylor et al. | |
| 6,036,685 A | 3/2000 | Mueller | |
| 6,039,733 A | 3/2000 | Buysse et al. | |
| 6,086,586 A | 7/2000 | Hooven | |
| 6,110,106 A | 8/2000 | MacKinnon et al. | |
| 6,161,543 A | 12/2000 | Cox et al. | |
| 6,235,025 B1 * | 5/2001 | Swartz et al. | 606/45 |
| 6,237,605 B1 | 5/2001 | Vaska et al. | |
| 6,245,065 B1 | 6/2001 | Panescu et al. | |
| 6,251,065 B1 | 6/2001 | Kochamba et al. | |
| 6,277,065 B1 | 8/2001 | Donofrio | |
| 6,292,678 B1 * | 9/2001 | Hall et al. | 600/374 |
| 6,309,349 B1 | 10/2001 | Bertolero et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,338,712 B2 | 1/2002 | Spence et al. | |
| 6,338,738 B1 | 1/2002 | Bellotti et al. | |
| 6,346,077 B1 | 2/2002 | Taylor et al. | |
| 6,350,229 B1 | 2/2002 | Borst et al. | |
| 6,352,534 B1 | 3/2002 | Paddock et al. | |
| 6,364,826 B1 | 4/2002 | Borst et al. | |
| 6,371,906 B1 | 4/2002 | Borst et al. | |
| 6,390,976 B1 | 5/2002 | Spence et al. | |
| 6,394,948 B1 | 5/2002 | Borst et al. | |
| 6,463,332 B1 | 10/2002 | Aldrich | |
| 6,464,630 B1 | 10/2002 | Borst et al. | |
| 6,482,151 B1 | 11/2002 | Vierra et al. | |
| 6,484,727 B1 * | 11/2002 | Vaska et al. | 128/898 |
| 6,511,416 B1 | 1/2003 | Green, II et al. | |
| 6,514,250 B1 | 2/2003 | Jahns et al. | |
| 6,522,905 B2 | 2/2003 | Desai | |
| 6,524,338 B1 | 2/2003 | Gundry | |
| 6,527,767 B2 | 3/2003 | Wang et al. | |
| 6,542,766 B2 * | 4/2003 | Hall et al. | 600/374 |
| 6,544,263 B2 | 4/2003 | Morgan et al. | |
| 6,595,989 B1 | 7/2003 | Schaer | |
| 6,599,237 B1 | 7/2003 | Singh | |
| 6,645,202 B1 | 11/2003 | Pless et al. | |
| 6,652,518 B2 | 11/2003 | Wellman et al. | |
| 6,758,809 B2 | 7/2004 | Briscoe et al. | |
| 6,849,075 B2 | 2/2005 | Bertolero et al. | |
| 6,890,295 B2 | 5/2005 | Michels et al. | |
| 6,893,437 B2 | 5/2005 | Swanson et al. | |
| 6,980,843 B2 * | 12/2005 | Eng et al. | 600/374 |
| 7,008,418 B2 * | 3/2006 | Hall et al. | 606/41 |
| 7,018,328 B2 | 3/2006 | Mager et al. | |
| 7,115,122 B1 | 10/2006 | Swanson | |
| 7,214,230 B2 | 5/2007 | Brock et al. | |
| 7,226,448 B2 | 6/2007 | Bertolero et al. | |
| 7,237,555 B2 | 7/2007 | Kochamba et al. | |
| 7,338,434 B1 | 3/2008 | Haarstad et al. | |
| 7,542,807 B2 | 6/2009 | Bertolero et al. | |
| 7,594,915 B2 | 9/2009 | Kochamba et al. | |
| 8,048,072 B2 * | 11/2011 | Verin et al. | 606/41 |
| 2002/0026094 A1 | 2/2002 | Roth | |
| 2002/0056460 A1 | 5/2002 | Boyd | |
| 2002/0068855 A1 | 6/2002 | Daniel et al. | |
| 2002/0099270 A1 | 7/2002 | Taylor et al. | |
| 2002/0099390 A1 | 7/2002 | Kaplan | |
| 2002/0177846 A1 | 11/2002 | Mulier et al. | |
| 2003/0009080 A1 | 1/2003 | Peng et al. | |
| 2003/0010346 A1 | 1/2003 | Paolitto et al. | |
| 2003/0060685 A1 | 3/2003 | Houser et al. | |
| 2003/0158463 A1 | 8/2003 | Julian et al. | |
| 2003/0158464 A1 | 8/2003 | Bertolero | |
| 2005/0010079 A1 | 1/2005 | Bertolero et al. | |
| 2005/0119653 A1 | 6/2005 | Swanson | |
| 2005/0119654 A1 | 6/2005 | Swanson et al. | |
| 2005/0240175 A1 | 10/2005 | Bertolero et al. | |
| 2006/0015165 A1 | 1/2006 | Bertolero et al. | |
| 2006/0155272 A1 | 7/2006 | Swanson | |
| 2007/0233226 A1 | 10/2007 | Kochamba et al. | |
| 2008/0294154 A1 * | 11/2008 | Ibrahim et al. | 606/13 |
| 2009/0048591 A1 | 2/2009 | Ibrahim et al. | |
| 2009/0076501 A1 | 3/2009 | Bertolero et al. | |
| 2009/0076537 A1 | 3/2009 | Bertolero | |
| 2009/0124847 A1 * | 5/2009 | Doty et al. | 600/10 |
| 2009/0163768 A1 | 6/2009 | Ibrahim et al. | |
| 2009/0281541 A1 | 11/2009 | Ibrahim et al. | |
| 2010/0036195 A1 * | 2/2010 | Bertolero et al. | 600/37 |

OTHER PUBLICATIONS

Faddis, Mitchell N. et al., "Novel, Magnetically Guided Catheter for Endocardial Mapping and Radiofrequency Catheter Ablation", *Circulation*, Dec. 3, 2002, pp. 2980-2985.

Jansen, Erik, et al., "Less Invasive off-pump CABG using a suction device for immobilization: The Octopus method," European Journal of Cardiothoracic surgery 12 (1997) pp. 406-412.

Kyoung-Ryul Chun, Julian et al., "Remote-controlled catheter ablation of accessory pathways: results from the magnetic laboratory", European Heart Journal (2007) 28, 190-195.

Pappone, Carlo et al., "Robotic Magnetic Navigation for Atrial Fibrillation Ablation", *JACC*, vol. 47, No. 7, Apr. 4, 2006, 2006:1390-400.

* cited by examiner

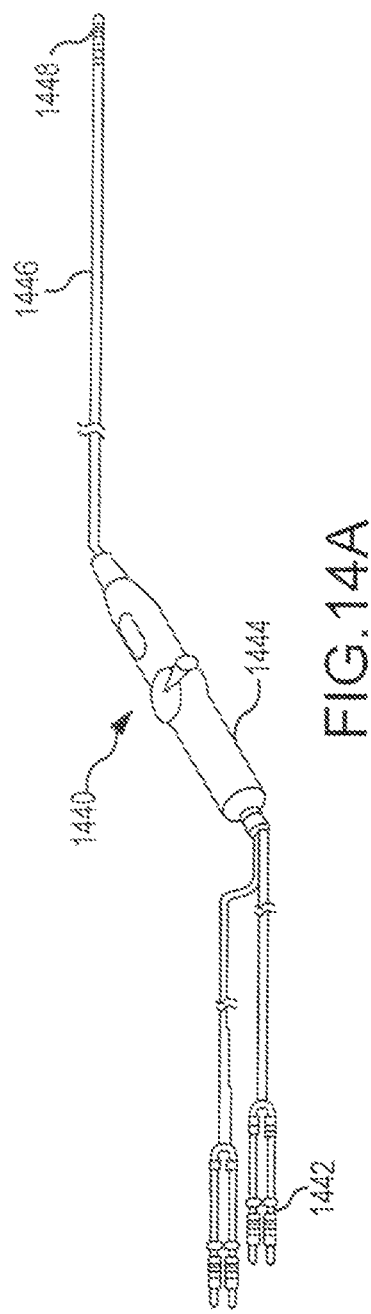
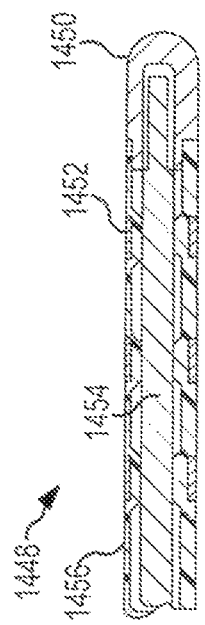
FIG. 14A
FIG. 14B

MAGNETIC NAVIGATION SYSTEMS AND METHODS

CROSS-REFERENCES TO RELATED APPLICATIONS

This application is a nonprovisional of, and claims the benefit of the filing date of, U.S. Provisional Patent Application No. 61/179,564, entitled "MAGNETIC NAVIGATION SYSTEMS AND METHODS," filed May 19, 2009 by Tamer Ibrahim et al., the entire disclosure of which is incorporated herein by reference for all purposes.

This application is related to U.S. patent application No. 60/939,201 filed May 21, 2007, U.S. Patent Application No. 61/015,472 filed Dec. 20, 2007, and U.S. patent application Ser. Nos. 12/124,743 and 12/124,766 filed May 21, 2008. The entire content of each of these filings is incorporated herein by reference for all purposes.

BACKGROUND OF THE INVENTION

Embodiments of the present invention related to medical devices and methods, and in particular to cardiac ablation systems and methods.

Atrial fibrillation (AF) is a common clinical condition, and presents a substantial medical issue to aging populations. AF is costly to health systems, and can cause complications such as thrombo-embolism, heart failure, electrical and structural remodeling of the heart, and even death.

For many years, the main treatment for atrial fibrillation (AF) involved pharmacological intervention. More recently, the focus has shifted toward surgical or catheter ablation options to treat or effect a cure for AF. The ablation techniques for producing lines of electrical isolation are now replacing the so-called Maze procedure. The Maze procedure uses a set of transmural surgical incisions on the atria to create fibrous scars in a prescribed pattern. This procedure was found to be highly efficacious but was associated with a high morbidly rate. The more recent approach of making lines of scar tissue with modern ablation technology has enabled the electro-physiologist or cardiac surgeon to create the lines of scar tissue more safely. Ideally, re-entrant circuits that perpetuate AF can be interrupted by the connected lines of scar tissue, and the goal of achieving normal sinus rhythm in the heart may be achieved.

Triggers for intermittent AF and drivers for permanent AF can be located at various places on the heart, such as the atria. For example, where triggers or drivers are located near the pulmonary veins, it follows that treatment may involve electrical isolation of the pulmonary veins.

Certain cardiac surgical procedures involve administering ablative energy to the cardiac tissue in an attempt to create a transmural lesion on the tissue. However, in some cases such methods may not be optimal due to the formation of incomplete lesions, which do not effectively create a conduction block in the tissue. Relatedly, some techniques may not provide the desired positioning of an ablation element relative to the tissue which is to be treated, or may only provide complicated and expensive approaches that attempt to maintain the desired positioning. For example, some proposed techniques cannot adequately apply ablation to the moving tissue of a beating heart. Hence, there continues to be a need for improved systems and methods that can simply and effectively deliver ablative energy to patient tissue in a uniform and reproducible manner.

Although these and other proposed treatments may provide real benefits to patients in need thereof, still further advances would be desirable. For example, it would be desirable to provide improved systems and methods for guiding and navigating various mechanisms that are used in endocardial ablation procedures. Embodiments of the present invention provide solutions that address the problems described above, and hence provide answers to at least some of these outstanding needs.

BRIEF SUMMARY OF THE INVENTION

Advantageously, embodiments of the present invention provide techniques for applying endocardial lesions to tissue at or near the pulmonary vein (PV) ostia and other locations of the heart, to cause or enhance conduction block at the junction of the PV and left atrium as well as other blocking lesions. Such techniques are well suited for use with patients presenting with paroxysmal (focal) atrial fibrillation. Exemplary embodiments involve the administration of precisely controlled ablative energy, or controlled power, to create reproducible, uniform transmural lesions during cardiac surgery. Such techniques enable rapid and effective ablative lesions in a variety of clinical situations, including endocardial and epicardial ablations. By forming the transmural ablations, surgeons are able to achieve conduction block in the patient. Advantageously, embodiments of the present invention can be used to create complete lesion sets and reliably produce transmural lesions on a beating heart. According to embodiments disclosed herein, transmural lesions across the atrial wall can be performed reliably and efficiently.

Embodiments also includes ablation systems having an ablation energy source for providing energy to the ablation device. An ablation energy source is typically suited for use with ablation apparatus as described herein using RF energy. With regard to RF ablation, a typical RF ablation system includes a RF generator which feeds current to an ablation device, including those described in this application, containing a conductive electrode for contacting targeted tissue. The electrical circuit can be completed by a return path to the RF generator, provided through the patient and a large conductive plate, which is typically in contact with the patient's back. Embodiments encompass ablation using RF electrodes, including single RF ablation electrodes. Although ablation energy is often described herein in terms of RF energy, it is understood that embodiments are not limited to such ablation modalities, and other kinds of ablation energy sources and ablation devices may be used. Hence, with regard to the ablation techniques disclosed herein, other suitable ablation elements or mechanisms, instead or in addition to an RF electrode, can be used. Embodiments of the present invention therefore encompass any of a variety of ablation techniques, including without limitation infrared lasers, high intensity focused ultrasound (HIFU), microwave, Cryoablation (killing or damaging the tissue by freezing), chemical or biological agents, radiation, and the like. In some cases, an ablation mechanism can include an ablation element that transmits or delivers RF energy to patient tissue. Optionally, suitable ablation elements can transmit or deliver infrared laser energy, high intensity focused ultrasound (HIFU) energy, microwave energy, Cryoablation energy, chemical agents, biological agents, radiation energy, and the like. Embodiments encompass ablation mechanisms having multiple ablation elements, such as multiple RF electrodes. According to some embodiments, an ablation element may include a monopolar electrode. Relatedly, an ablation element may include a bipolar electrode. Any of these modalities is well suited for use in endocardial ablation techniques resulting in electrical isolation and transmurality.

With the appropriate use of magnetic elements, it is possible to create endocardial lesions by dragging an ablation element along the endocardium, within the heart. A guiding mechanism disposed on the outside of the heart chamber can be used to maneuver an ablation mechanism disposed within the heart chamber. Advantageously, such techniques can enhance contact between an ablative element and the endocardial tissue or inner lining of the heart, even in a beating heart. Permanent magnets are well suited for such use, although electromagnets can also be used.

In a first aspect, embodiments of the present invention encompass method of forming a lesion on an endocardial tissue of a patient's heart. Exemplary methods can include placing an ablation assembly inside of the heart and adjacent to the endocardial tissue, and placing a guiding assembly outside of the heart. The ablation assembly can include an ablation element and a first attraction element, and the guiding assembly can include a second attraction element. Often, a magnetic attraction is present between the first and second attraction elements. Methods can also include forming the ablation on the endocardial tissue of the patient's heart with the ablation element of the ablation assembly. In some cases, the first attraction element includes a magnetized element. In some cases, the second attraction element includes a magnetized element. Methods may also involve moving the second attraction element of the guiding assembly relative to the patient's heart, so as to effect a corresponding movement of the ablation element of the ablation assembly. According to some embodiments, the ablation element includes a radiofrequency ablation element, an infrared laser ablation element, a high intensity focused ultrasound ablation element, a microwave ablation element, a cryoablation ablation element, a chemical agent ablation element, a biological agent ablation element, a radiation ablation element, or the like. The ablation element may for example include a monopolar electrode or a bipolar electrode. In some cases, a guiding assembly includes an elongate wand, and the second attraction element is coupled with a distal portion of the elongate wand. The ablation assembly may include an elongate catheter, and the first attraction element can be coupled with a distal portion of the elongate catheter. Optionally, the ablation element can be coupled with the distal portion of the elongate catheter.

In another aspect, embodiments of the present invention encompass systems for forming a lesion on an endocardial tissue of a patient's heart. Exemplary systems can include an ablation assembly having an ablation element and a first attraction element, and a guiding assembly having a second attraction element, such that a magnetic attraction is present between the first and second attraction elements or the first and second attraction elements are magnetically attractable toward each other. In some cases, the first attraction element includes a magnetized element. In some cases, the second attraction element includes a magnetized element. According to some embodiments, the ablation element includes a radiofrequency ablation element, an infrared laser ablation element, a high intensity focused ultrasound ablation element, a microwave ablation element, a cryoablation ablation element, a chemical agent ablation element, a biological agent ablation element, a radiation ablation element, or the like. The ablation element may for example include a monopolar electrode or a bipolar electrode. In some cases, a guiding assembly includes an elongate wand, and the second attraction element is coupled with a distal portion of the elongate wand. The ablation assembly may include an elongate catheter, and the first attraction element can be coupled with a distal portion of the elongate catheter. Optionally, the ablation element can be coupled with the distal portion of the elongate catheter.

For a fuller understanding of the nature and advantages of the present invention, reference should be had to the ensuing detailed description taken in conjunction with the accompanying drawings.

BRIEF DESCRIPTION OF THE DRAWINGS

FIGS. 14A-14D illustrate aspects of ablation treatment systems and methods according to embodiments of the present invention.

DETAILED DESCRIPTION OF THE INVENTION

Figure 1:
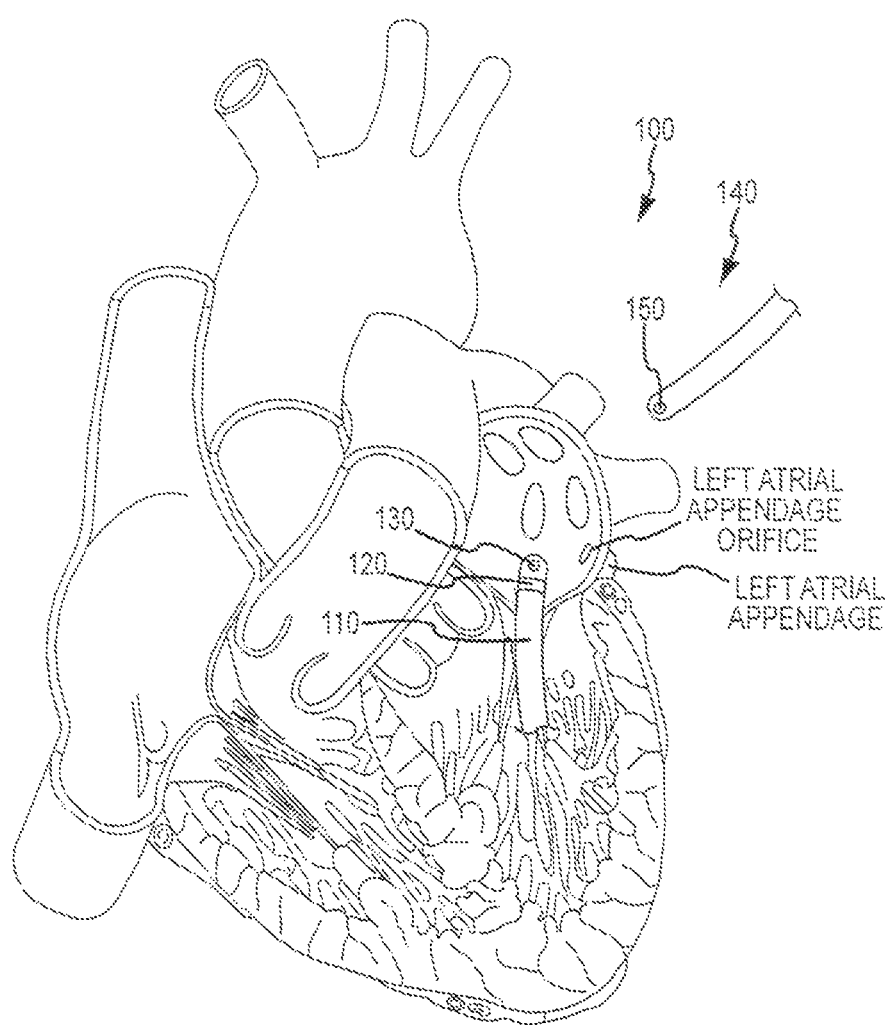
FIG. 1 illustrates aspects of ablation treatment systems and methods according to embodiments of the present invention.

Embodiments of the present invention encompass magnetic navigation systems and methods for performing endocardial ablation in a patient in need thereof. For example, such techniques are well suited for treating patients who present with atrial fibrillation and other electrical abnormalities of the heart such as incessant ventricular tachycardia. Cardiac conditions such as these can lead to thrombo-embolisms, heart failure, and other complications in a patient. These treatment approaches provided herein can result in electrical isolation or blockage between various portions of cardiac tissue, optionally via the creation of transmural ablations at selected locations on the endocardium. For example, methods and systems can be used to create scars that produce lines of electrical isolation, so as to inhibit or prevent electrical activity which may otherwise lead to or perpetuate atrial fibrillation, or so as to promote or maintain normal sinus rhythm in the patient. In some cases, these techniques can be used to form lesions at or near the pulmonary veins, the left atrial appendage, or the mitral valve, for example. Techniques can be used to treat patients presenting paroxysmal or intermittent atrial fibrillation, as well as persistent or long-lasting persistent atrial fibrillation.

In some cases, systems and methods can involve placing an ablation assembly inside of the heart and adjacent to the endocardial tissue, and placing a guiding assembly outside of the heart. The ablation assembly can include an ablation element and a first attraction element, and the guiding assembly can include a second attraction element. In use, a magnetic attraction is present between the first and second attraction elements. The techniques typically involve forming an ablation on the endocardial tissue of the patient's heart with the ablation element of the ablation assembly.

The attraction elements can include magnets, magnetized or magnetizable materials or objects, magnetically attractable materials or objects, materials or objects that produce a magnetic field, materials or objects that are attracted to or influenced by a magnetic field, and the like. Attraction elements can include devices such as magnets. For example, a magnetic member may include a combination of neodymium, iron, and boron. In some cases, a magnetic member may be nickel plated. In some cases, an attraction element can include a hard or permanent magnet that retains its magnetization or magnetism. In some cases, an attraction element can include a soft or impermanent magnet that loses its memory of previous magnetizations. Optionally, an attraction element can include an electromagnet. In some cases, an attraction element can include a material which is not magnetized, but is attracted to a magnet, such as iron or a ferrous or ferromagnetic material. Hence, any of a variety of magnets, magnetizable or magnetized materials, or magnetically attractable materials, may be used. According to some embodiments, an attraction element may include a nonferrous or paramagnetic material such as magnesium or molybdenum.

By placing the ablation assembly and the guiding assembly in proximity with each other, such that their respective attraction elements attract, a surgeon or operator can create lesions on the endocardium by using the guiding assembly to move the ablation element to various locations and forming ablations on the inside of the heart. In some cases, an ablation assembly can include a catheter with an ablation element on the distal portion of the catheter. Such methods are well suited for use in treating a patient with a beating heart, as the magnetic attraction or force between the attraction elements can serve to maintain placement of the ablation element relative to the moving cardiac tissue.

Accordingly, in one embodiment, an operator can use the guiding element similar to a pen or writing instrument, effectively drawing on the outside of the heart while the ablation element forms a lesion on the endocardium using monopolar RF and a return path to one or more grounding pads placed on the patient's skin. In an alternative embodiment, the guiding element itself serves as an ablation element and a bipolar ablation is performed from the epicardial ablation element to the endocardial ablation element. In some embodiments involving a bipolar mode of ablation, a transmural ablation lesion may be more assured because the heating pattern from the RF is more constrained and the lesion grows from both the endocardium and the epicardium. In still another embodiment, the epicardial guide element includes a monopolar ablation element, and the endocardial magnetic tip is not directly involved in the ablation process. The magnetic tip provides a means to move the epicardial ablation element or simply assures good contact of the ablation element to the epicardium. Hence, a guiding assembly can be placed inside of the heart chamber, and can be magnetically attracted to an ablation assembly disposed on the exterior of the heart. Advantageously, such techniques may avoid or reduce the possibility of coagulating blood within a chamber of the heart, and hence provide a beneficial safety feature.

Turning now to the drawings, FIG. 1 illustrates an ablation treatment system 100 according to embodiments of the present invention. Treatment system 100 includes an ablation assembly 110 having an ablation element 120 and a first attraction element 130. Treatment system 100 also includes a guiding assembly 140 having a second attraction element 150. When in sufficiently close proximity, a magnetic attraction is present between the first and second attraction elements. Ablation element 120 may include an RF electrode, for example, and attraction element 130 may include a magnet.

Figure 1A:
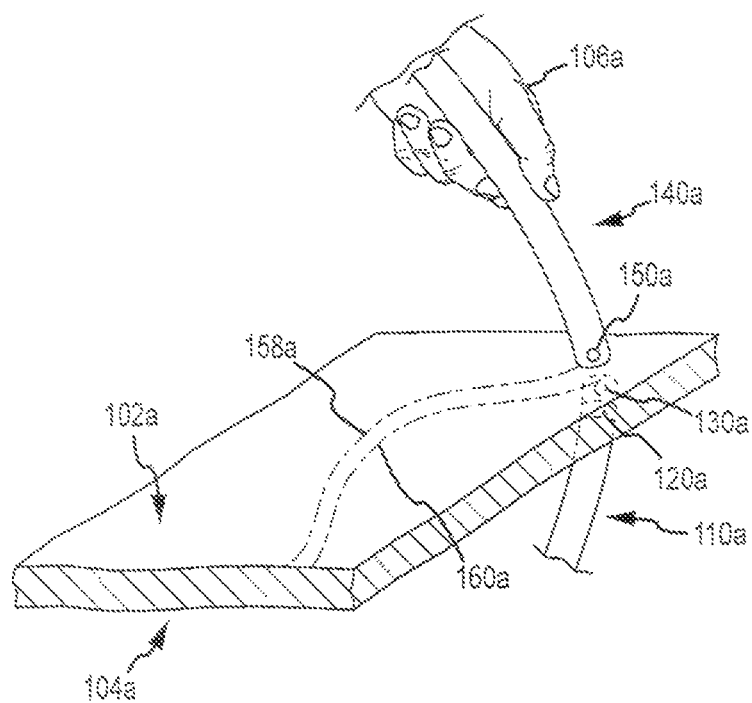
FIGS. 1A-1H illustrate aspects of ablation treatment systems and methods according to embodiments of the present invention.
Figure 1B:
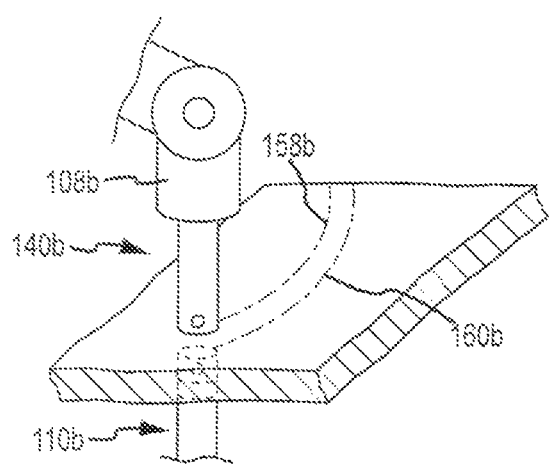

As illustrated in FIGS. 1A and 1B, lesions may be created by placing guiding assembly 140a on or near the exterior of the heart and drawing or tracing a pattern proximate to the surface of the heart or cardiac tissue 102a as illustrated by guiding pattern 158a. Due to attraction between first attraction element 130a of ablation assembly 110a and second attraction element 150a of guiding assembly 140a, a corresponding pattern can be traced on the interior surface of the heart or cardiac tissue 104a, as illustrated by ablation pattern 160a, and a lesion can be created along the ablation pattern by ablation element 120a. Furthermore, the procedures may be performed while the patient's heart is beating. Likewise, the procedures may be performed manually or with the assistance of operative equipment. For example, as illustrated in FIG. 1A, in some cases a surgeon or operator may create the lesions by hand 106a using guiding assembly 140a similar to a pen or other writing instrument to draw or trace a pattern on or near the exterior of the heart. Optionally, aspects of the procedure may be at least partially automated through the use of robotic or other equipment. Robotic or other equipment may be used to assist the surgeon or operator in tracing or drawing the pattern or may be used solely to trace or draw the pattern according to a set of instructions, optionally provided by a computer. For example, FIG. 1B illustrates a robotic unit 108b operating guiding assembly 140b to trace or draw guiding pattern 158b proximate to the surface of a heart. Consequently, ablation assembly 110b can trace a corresponding ablation pattern 160b on the interior of the heart due to attraction between guiding assembly 140b and ablation assembly 110b. Embodiments of the present invention may encompass the use of any of a variety of visualization guidance members to assist the operator in performing a medical procedure, including endoscopic visualization devices, fluoroscopy visualization devices, ultrasonic visualization devices, and the like. Exemplary visualization members are discussed in U.S. patent application Ser. No. 10/310,675 filed Dec. 4, 2002, the content of which is incorporated herein by reference. Treatment systems may include mechanisms containing an attraction element, an ablation element, and a temperature sensing element, as discussed elsewhere herein.

Figure 1C:
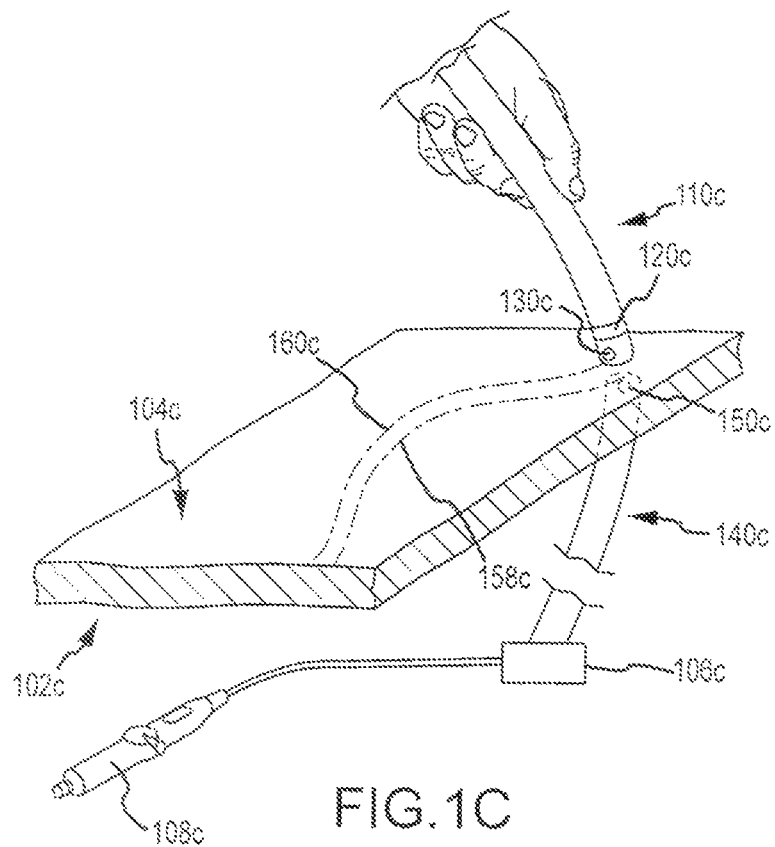
Figure 1D:
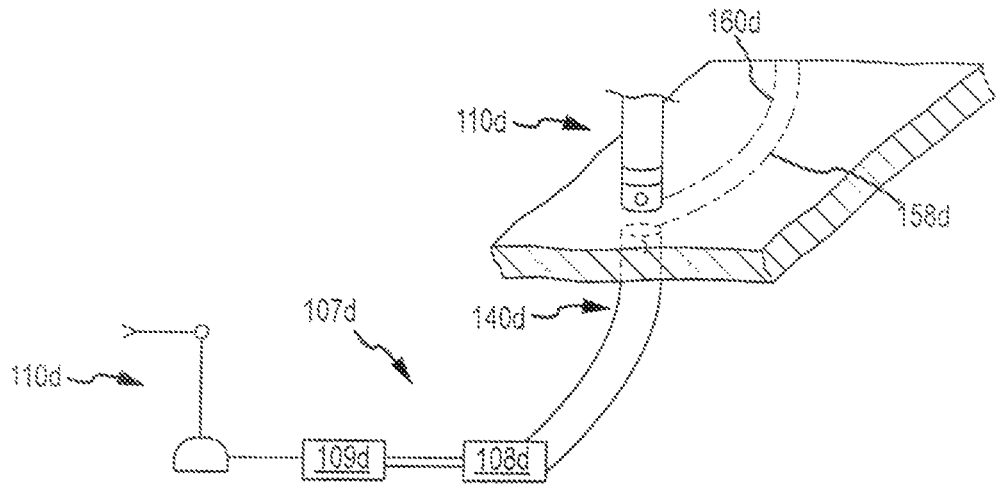

FIGS. 1A and 1B illustrate an endo-monopolar approach, whereby ablation energy is provided by ablation element 120a in a monopolar format on the endocardial or interior surface of the heart tissue 104a. Embodiments of the present invention also encompass epi-monopolar approaches, as well as bipolar approaches. For example, FIGS. 1C and 1D illustrate aspects of an epi-monopolar approach. Advantageously, epi-monopolar techniques may reduce the risk of stroke in a patient undergoing an ablation treatment, as the ablation energy is applied to the exterior of the heart. There is less opportunity for ablation-induced clots to form on the inside of the patient's heart and be dispersed throughout the patient's circulation. As shown in FIG. 1C, lesions may be created by placing guiding assembly 140c on or near the interior of the heart and drawing or tracing a pattern proximate to the surface of the heart or cardiac tissue 102c as illustrated by guiding pattern 158c. Due to attraction between first attraction element 130c of ablation assembly 110c and second attraction element 150c of guiding assembly 140c, a corresponding pattern can be traced on the exterior surface of the heart or cardiac tissue 104c, as illustrated by ablation pattern 160c, and a lesion can be created along the ablation pattern by ablation element 120c. Furthermore, the procedures may be performed while the patient's heart is beating. Likewise, the procedures may be performed manually or with the assistance of operative equipment. For example, as illustrated in FIG. 1C, in some cases a surgeon or operator may create the lesions using a steerable catheter mechanism 106c that is coupled with or that includes guiding assembly 140c to draw or trace a pattern on or near the interior of the heart. As depicted here, a handle 108c is coupled with steerable catheter mechanism 106c, which can allow a surgeon or user to perform a robotically enhanced ablation procedure. Optionally, aspects of the procedure may be at least partially automated through the use of robotic or other equipment. Robotic or other equipment may be used to assist the surgeon or operator in tracing or drawing the pattern or may be used solely to trace or draw the pattern according to a set of instructions, optionally provided by a computer. For example, FIG. 1D illustrates a robotically aided catheter or remote control system 107d having a guiding assembly 140d in operative association with a mechanically driveable system 108d, which is in operative association with a processor or computer controller 109d, which in turn is in operative association with a surgeon interface 110d. Such remote control systems or robotically assisted catheter mechanisms which are well suited for use in embodiments of the present invention are described in U.S. Pat. No. 7,214,230, the content of which is incorporated herein by reference. Guiding assembly 140d can be moved so as to trace or draw guiding pattern 158d proximate to the interior surface of a heart. Consequently, ablation assembly 110d can trace a corresponding ablation pattern 160d on the exterior of the heart due to attraction between guiding assembly 140d and ablation assembly 110d. In an exemplary monopolar technique, a delivery electrode is used to administer the ablative energy, and the return electrode is attached or coupled with the patient's skin.

Any of a variety of robotic assisted techniques can be used to manipulate a guiding assembly or catheter. For example, U.S. Pat. No. 7,214,230, incorporated herein by reference, describes a remote control flexible instrument system which can be used to robotically assist or define catheter or sheath manipulations. Embodiments of the present invention may encompass robotic assisted technologies such as those provided by Hansen Medical, Inc. (Mountain View, Calif.).

Advantageously, bipolar techniques may reduce the risk of stroke in a patient undergoing an ablation treatment, as ablation energy is applied to the exterior of the heart. There is less opportunity for ablation-induced clots to form on the inside of the patient's heart and be dispersed throughout the patient's circulation. In an exemplary bipolar system, a first electrode is disposed on one side of the tissue, for example on the epicardial surface of the heart, and a second electrode is disposed on the other side of the tissue, for example on the endocardial surface of the heart. Current is drawn from one side to the other; the sending electrode is located close to the return electrode, hence minimizing a spreading of the current. Current flowing through the tissue consequently heats the tissue from both sides, so as to efficiently create a transmural lesion. For example, application of ablative energy between a delivery electrode and a return electrode can heat the tissue to greater than about 50 degrees Celsius. In some bipolar embodiments, an active or guiding element is disposed on the external surface, and a passive or guidable element is disposed on the internal surface. Optionally, an active or guiding element can be disposed on the internal surface, and a passive or guidable element can be disposed on the external surface. In a bipolar ablation, RF energy typically goes both ways, between the endocardium and the epicardium.

Figure 1E:
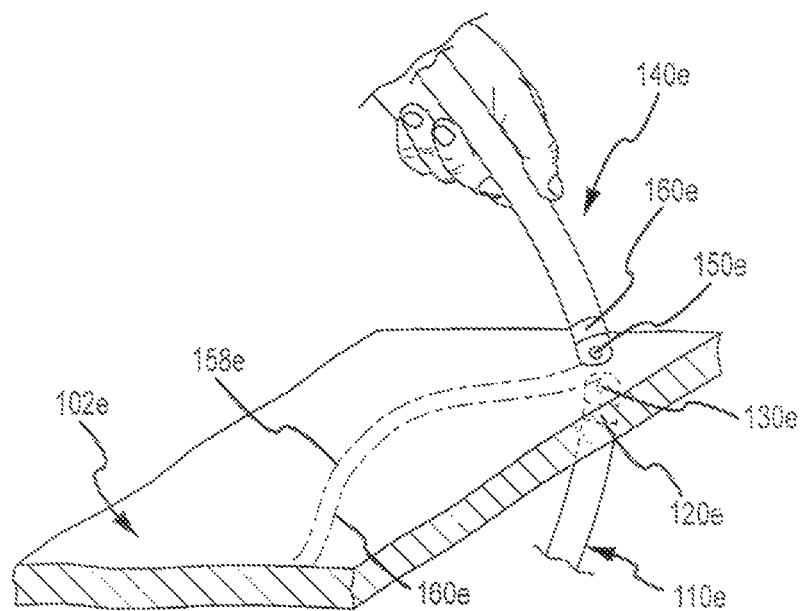
Figure 1F:
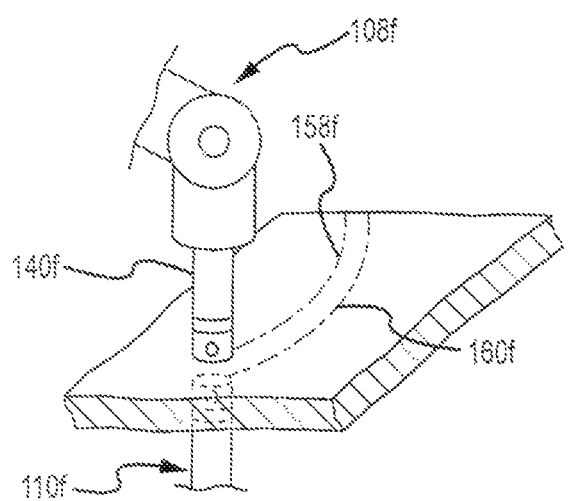

FIGS. 1E and 1F illustrate aspects of a bipolar approach according to embodiments of the present invention. As shown in FIG. 1E, lesions may be created by placing guiding assembly or an outer bipolar ablation assembly 140e on or near the exterior of the heart and drawing or tracing a pattern proximate to the surface of the heart or cardiac tissue 102e as illustrated by guiding pattern 158e. As shown here, outer bipolar ablation assembly includes an attraction element 150e and an ablation element 160e. Due to attraction between first attraction element 130e of ablation assembly 110e and second attraction element 150e of guiding assembly 140e, a corresponding pattern can be traced on the exterior surface of the heart or cardiac tissue 104e, as illustrated by inner ablation pattern 160e. Relatedly, guiding pattern 158e can also represent an outer ablation pattern. Hence, a transmural ablation can be created by the external ablation element 160e and the internal ablation element 120e in a bipolar fashion. Furthermore, the procedures may be performed while the patient's heart is beating. Likewise, the procedures may be performed manually or with the assistance of operative equipment. FIG. 1F illustrates a robotic unit 108f operating guiding assembly 140b to trace or draw guiding pattern 158f proximate to the surface of a heart. Due to attraction between an external attraction element of the external assembly 140f and an internal attraction element of the internal assembly 110f, a corresponding pattern can be traced on the interior surface of the heart or cardiac tissue, as illustrated by inner pattern 160f. Relatedly, guiding pattern 158f can also represent an outer ablation pattern. Hence, a transmural ablation can be created by the external ablation element of the external assembly 140f and the internal ablation element of the internal assembly 110f in a bipolar fashion.

Figure 1G:
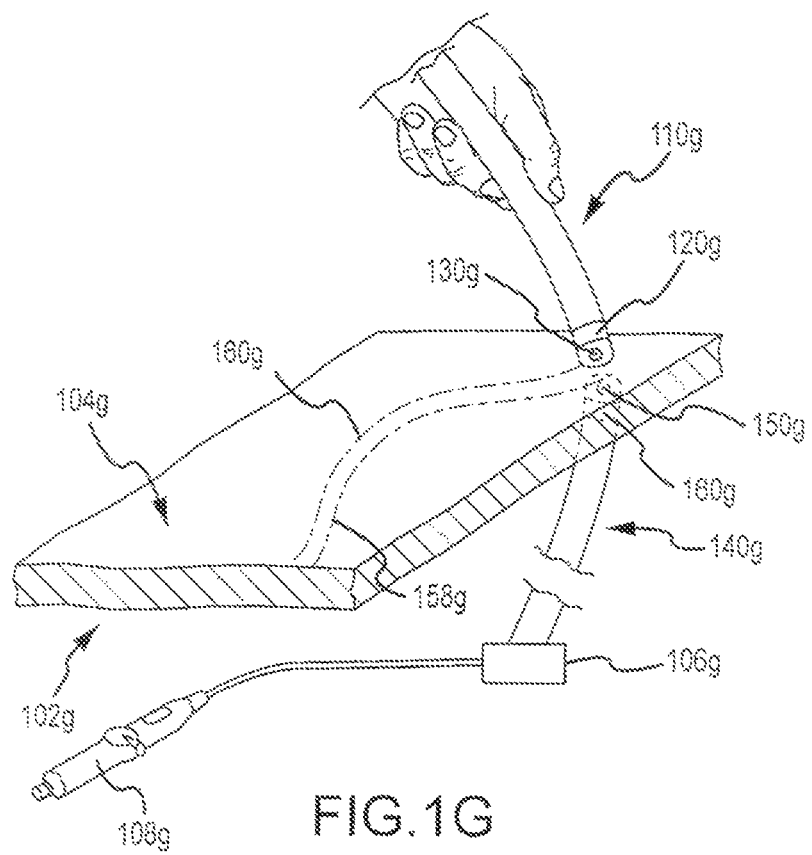
Figure 1H:
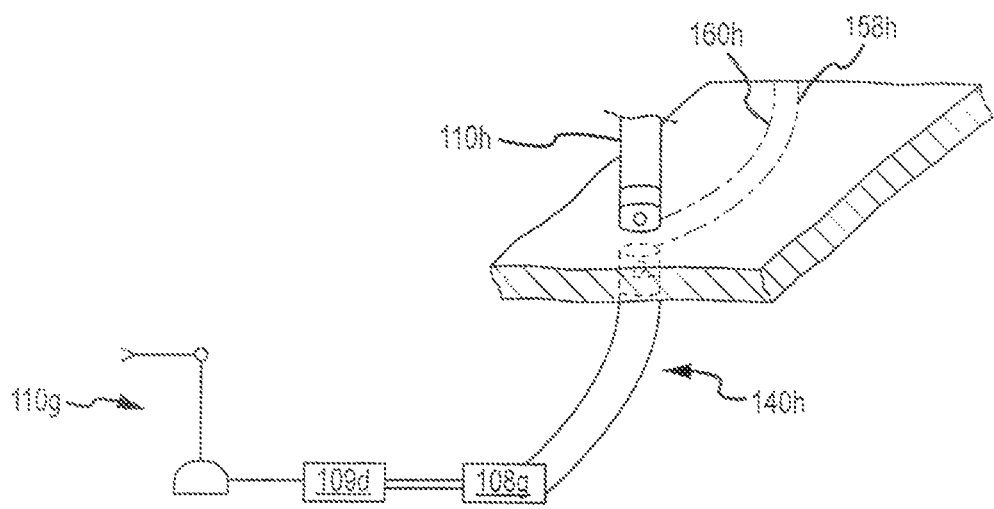

FIGS. 1G and 1H illustrate aspects of other bipolar approaches. As shown in FIG. 1G, lesions may be created by placing guiding assembly 140g on or near the interior of the heart and drawing or tracing a pattern proximate to the surface of the heart or cardiac tissue 102g as illustrated by guiding pattern 158g. Due to attraction between first attraction element 130g of ablation assembly 110g and second attraction element 150g of guiding assembly 140g, a corresponding pattern can be traced on the exterior surface of the heart or cardiac tissue 104g, as illustrated by external ablation pattern 160g. Relatedly, guiding pattern 158g can also represent an inner ablation pattern. Hence, a transmural ablation can be created by the external ablation element 120g and the internal ablation element 160g in a bipolar fashion. As shown here, external ablation element 120g or internal ablation element 160g may include a metallic ring, band, or sleeve. Optionally, the ablation element or electrode can encircle or surround an attraction mechanism. In some cases a surgeon or operator may create the lesions using a steerable catheter mechanism 106g that is coupled with or that includes guiding assembly 140g to draw or trace a pattern on or near the interior of the heart. As depicted here, a handle 108g is coupled with steerable catheter mechanism 106g, which can allow a surgeon or user to perform a robotically enhanced ablation procedure.

Optionally, aspects of the procedure may be at least partially automated through the use of robotic or other equipment. Robotic or other equipment may be used to assist the surgeon or operator in tracing or drawing the pattern or may be used solely to trace or draw the pattern according to a set of instructions, optionally provided by a computer. For example, FIG. 1H illustrates a robotically aided catheter or remote control system 107h having a guiding assembly 140h in operative association with a mechanically driveable system 108h, which is in operative association with a processor or computer controller 109h, which in turn is in operative association with a surgeon interface 110h. Such remote control systems or robotically assisted catheter mechanisms which are well suited for use in embodiments of the present invention are described in U.S. Pat. No. 7,214,230, the content of which is incorporated herein by reference. Guiding assembly 140h can be moved so as to trace or draw guiding pattern 158h proximate to the interior surface of a heart. Consequently, outer ablation assembly 110h can trace a corresponding external ablation pattern 160h on the exterior of the heart due to attraction between guiding assembly 140d and ablation assembly 110h. Relatedly, guiding pattern 158h can also represent an inner ablation pattern. Hence, a transmural ablation can be created by the external ablation element of external ablation assembly 110h and the internal ablation element of internal ablation assembly 140h in a bipolar fashion.

As depicted in embodiments provided in FIGS. 1A-1H, treatment systems may include a driving or leading element disposed either externally at the epicardial surface, or internally at the endocardial surface. Similarly, a passive or following element can be disposed either internally at the endocardial surface, or externally at the epicardial surface. Embodiments of the present invention encompass systems which provide a monopolar ablation element at the endocardial surface, as depicted in FIG. 1A. Embodiments of the present invention also encompass systems which provide a monopolar ablation element at the epicardial surface, as depicted in FIG. 1C. Embodiments of the present invention further encompass systems which provide a bipolar ablation elements at the epicardial and endocardial surfaces, as depicted in FIG. 1E. Any of the configurations described here are well suited for use with the raceway or tracking systems described in FIGS. 5A-6D. What is more, any of the embodiments depicted here can incorporate power delivery modalities wherein the power delivered is based on temperature feedback control of power.

In a bipolar ablation procedure, it may be desirable to perform temperature sensing at or near the epicardium when determining how much power is to be delivered for the ablation. For example, temperature control can be modulated based on temperatures sensed at or near an epicardial electrode. In general, an electrode disposed at or near the endocardium will be exposed to flowing blood in the heart and therefore will be cooler than an electrode disposed at or near the epicardium. It may be desirable to control the ablation power based on the tissue exhibiting the higher temperature, which is most often the epicardium. Typically, during an ablation, heat flows into the tissue being ablated, more so than into the surrounding environment.

According to some embodiments, control of ablative power administration is based on epicardial temperature sensing. In some cases, the size or surface area of an epicardial electrode is larger than the size or surface area of an endocardial electrode, and temperature sensing can be performed at or near the endocardial surface. For example, the surface area of the epicardial electrode may be twice the surface area of the endocardial electrode. In some cases, it may be desirable to place a temperature sensor on the smaller of two differently sized electrodes, as the current density is likely to be greater on a smaller electrode hence providing a higher temperature. It may be desirable to maintain the temperature at or near the endocardial surface below a selected value (e.g. between about 50 and 60 degrees Celsius) so as to minimize the possibility of clot formation, while providing sufficient heat to ablate the tissue. Relatedly, it may be desirable to control the ablative energy administered based on the greater of the epicardial temperature and the endocardial temperature. Optionally, it is possible to predetermine which of the epicardial or endocardial surface temperatures will be greater during a treatment, and subsequently control the power administered during the treatment based on the surface having the greater predetermined temperature. In some cases, it is possible to perform temperature sensing at or near both the epicardial and endocardial surfaces. In some cases, it is possible to predict or predetermine the temperature at or near the epicardial surface based on the sensed temperature at or near the endocardial surface. In some cases, it is possible to predict or predetermine the temperature at or near the endocardial surface based on the sensed temperature at or near the epicardial surface. According to some embodiments, two or more temperature sensors are used to monitor temperatures of the epicardial and endocardial surfaces, and ablative power is administered so as to maintain a selected temperature differential between the epicardial and endocardial surfaces. For example, techniques may involve the modulation or administration of power to a bipolar ablation device so that epicardial tissue temperature does not exceed an amount that is about 10 degrees Celsius higher than the endocardial tissue temperature. Optionally, techniques may involve the modulation or administration of power to a bipolar ablation device so that epicardial tissue temperature is maintained at a temperature that is about 10 degrees Celsius higher than the endocardial tissue temperature. In some bipolar embodiments, control of ablative power is based on the epicardial temperature, the endocardial temperature, or both.

In addition to utilizing radiofrequency (RF) ablation modalities, embodiments of the present invention can incorporate any of a variety of ablation techniques, including without limitation microwave, laser energy, high intensity focused ultrasound (HIFU), and other heating technologies. Exemplary embodiments which include magnetic navigation and temperature sensing for RF ablation mechanisms are depicted at, for example, FIG. 11, as discussed elsewhere herein.

Although in many instances it is desirable to position an endocardial ablation or guiding element via an arterial access route, such as through the femoral artery, it is understood that in some instances an endocardial ablation or guiding element can be directly inserted into the left atrium, for example during a medical procedure that involves opening up the left atrium itself. Bipolar ablation modalities described herein are well suited for such procedures.

Figure 2:
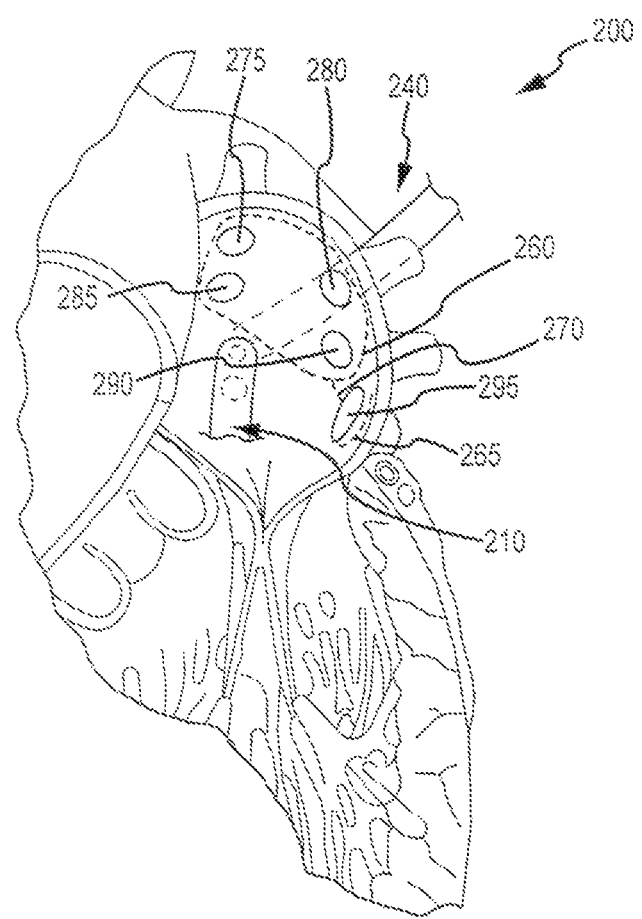
FIG. 2 illustrates aspects of ablation treatment systems and methods according to embodiments of the present invention.
Figure 3:
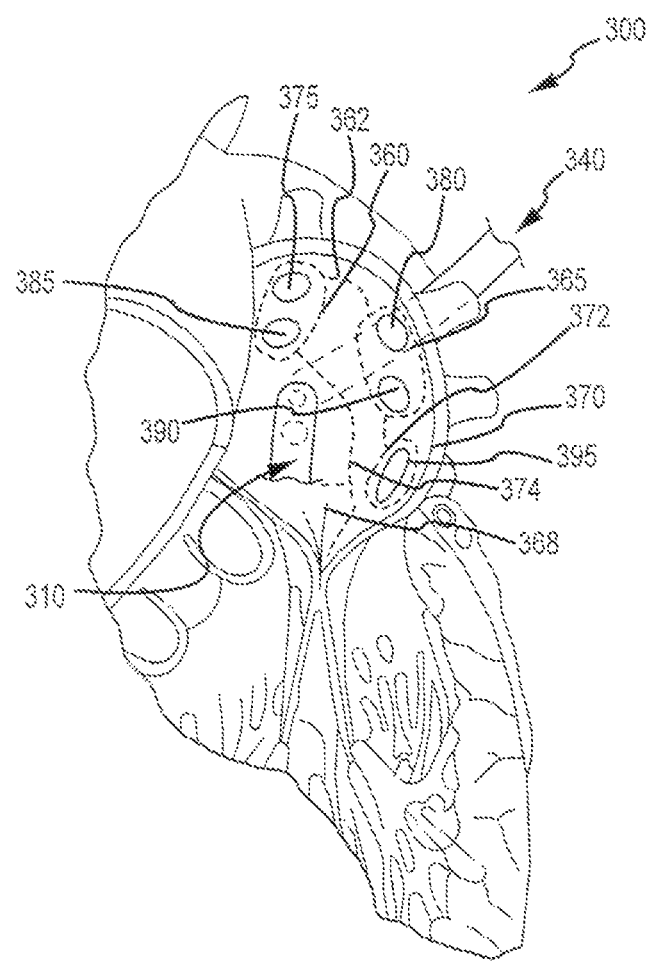
FIG. 3 illustrates aspects of ablation treatment systems and methods according to embodiments of the present invention.
Figure 4:
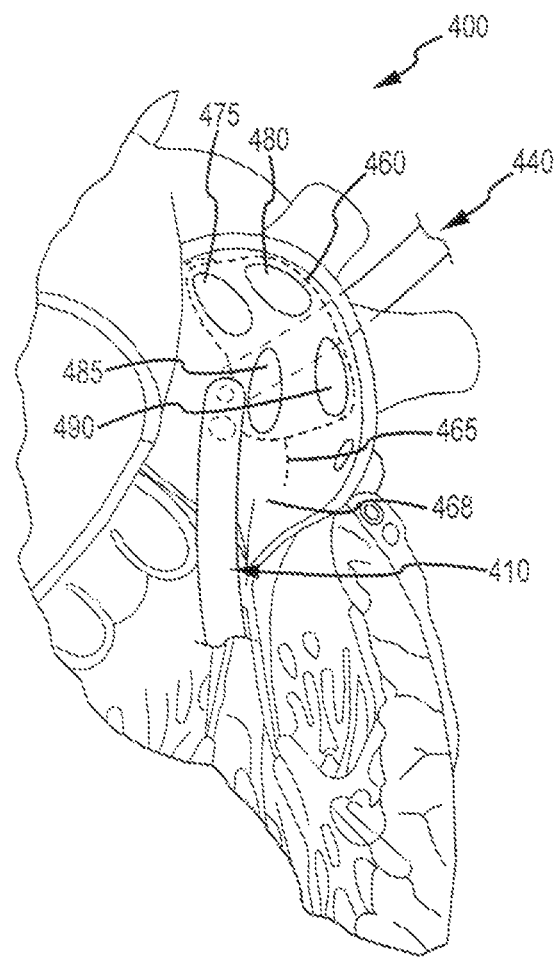
FIG. 4 illustrates aspects of ablation treatment systems and methods according to embodiments of the present invention.

FIGS. 2-4 illustrate the use of treatment systems having ablation assemblies and guiding assemblies in accordance with the embodiments of the present invention. The figures further illustrate several operative procedures that may be employed to create a lesion formation on the endocardial tissue of the heart. A lesion formation, which may also be referred to as a lesion, may include the creation of a single lesion, a series of associated lesions, multiple lesions such as a pair of parallel lesions, a set of lesions, a series of lesions, and the like. Lesions can be formed in accordance with any of the procedures described herein. In some cases, lesions may be partially or fully transmural. For example, a lesion may extend partially through, or fully through, the thickness of a tissue or organ wall. The term lesion may refer to the volume of tissue rendered permanently electrically unresponsive, most commonly due to irreversible thermal injury. Eventually the affected tissue becomes scar tissue. Because of the destructive change in the tissue, the lesion blocks the transmission of tissue excitation forcing the conduction pathway of the excitation waveform to either go around the lesion or to terminate at the lesion site.

In some cases, the treatment system may be used to create a single lesion that substantially encloses or encircles all the pulmonary veins or multiple lesions that each enclose or encircle one or more of the pulmonary veins. Furthermore, additional lesions may be created that concern other areas of the heart such as the left atrial appendage and the mitral valve.

FIG. 2 illustrates treatment system 200 in use to create a lesion that substantially encloses or encircles the ostia of the right and left superior pulmonary vein, 275 and 280 respectively, and the ostia of the right and left inferior pulmonary veins, 285 and 290 respectively. Treatment system 200 can be used to create an additional lesion stemming from a lesion near the pulmonary veins and extending toward the left atrial appendage orifice 295. A lesion substantially enclosing an ostium of a pulmonary vein may be created by placing guiding assembly 240 at or near one of a pulmonary vein and tracing or drawing a loop around the periphery of one or more pulmonary veins. As previously described, due to an attraction between guiding assembly 240 and ablation assembly 210, a corresponding pattern can be traced on the interior of the heart, as illustrated by ablation pattern 260, and a lesion can be created along ablation pattern 260 by an ablation element 230 of ablation assembly 210. Typically, ablation assembly 210 is advanced through the atrial septum, when traversing from the right atrium to the left atrium.

In a similar manner an additional lesion may be created that stems from a lesion near or enclosing a pulmonary vein ostium and that extends toward left atrial appendage orifice 295 by placing guiding assembly 240 at or near the left inferior pulmonary vein 290, for example, and tracing or drawing a path 270 toward left atrial appendage orifice 295. As previously described, a corresponding pattern is traced on the interior of the heart, as illustrated by ablation pattern 270, and a lesion can be created along the ablation pattern. In some cases, when the lesion is at or in close proximity with left atrial appendage orifice 295, it may be made to fork or "T." For example, the lesion may be made to fork or "T" along ablation pattern 265.

In some cases, it may be difficult to ablate between the right pulmonary veins, or between the left pulmonary veins. Hence, it may be desirable to ablate around the right pulmonary veins collectively, or around the left pulmonary veins collectively, or both. The left atrial appendage may be part of a re-entrant circuit, and a treatment can involve electrically isolating the left atrial appendage by ablating it, by sewing it shut, or by severing it.

FIG. 3 illustrates use of treatment system 300 to create multiple lesions enclosing the pulmonary veins and about other areas of the heart. For example, a lesion can enclose or encircle the ostia of the right and left superior pulmonary veins, 375 and 380 respectively. Similarly, a lesion can enclose or encircle the ostia of the right and left inferior pulmonary veins, 385 and 390 respectively. Optionally, a lesion may enclose or encircle a left atrial appendage orifice 395. A lesion may also extend toward the mitral valve 368.

In accordance with procedures described herein, a lesion substantially enclosing the right superior and inferior pulmonary veins, 375 and 385 respectively, may be created by positioning guiding assembly 340 at or near one of the right pulmonary veins and tracing or drawing a loop around the periphery of both the right superior and inferior pulmonary veins such that corresponding ablation pattern 360 is traced on the interior of the heart by ablation assembly 310. In a similar manner, a lesion substantially enclosing the left superior and inferior pulmonary veins, 380 and 390 respectively, may be created by placing guiding assembly 340 at or near one of the left pulmonary veins and tracing or drawing a loop around the periphery of both the left superior and inferior pulmonary veins such that corresponding ablation pattern 365 is traced on the interior of the heart by ablation assembly 310. The separate lesions enclosing each of the right and left pulmonary veins may then be associated or connected by placing the guiding assembly near one of the lesions and tracing or drawing a path toward the other lesion, thereby connecting both lesions. For example, the associating lesion may be created along ablation pattern 362.

Furthermore, in accordance with procedures described herein, a lesion substantially enclosing the left atrial appendage orifice 395 may be created and associated with the lesion enclosing the inferior pulmonary veins by tracing or drawing a loop and path that correspond with ablation patterns 370 and 372 respectively. Likewise, an additional lesion may be created that stems from a lesion that encloses either of the inferior pulmonary veins and that extends substantially to the mitral valve 368 by placing the guiding assembly at or near the lesion enclosing the inferior pulmonary vein and tracing or drawing a path toward the mitral valve 368 that corresponds with ablation pattern 374. This lesion may be made to fork or "T" along ablation pattern 374 when the lesion is at or in close proximity to the mitral valve 368. Ablation pattern 374 may extend to connect with ablation pattern 360 which encircles the right pulmonary veins.

In accordance with procedures described herein, a lesion substantially enclosing the right and left superior pulmonary veins, 375 and 380 respectively, may be created by positioning guiding assembly 340 at or near one of the superior pulmonary veins and tracing or drawing a loop around the periphery of both the right and left superior pulmonary veins such that corresponding ablation pattern is traced on the interior of the heart by ablation assembly 310. In a similar manner, a lesion substantially enclosing the right and left inferior pulmonary veins, 385 and 390 respectively, may be created by placing guiding assembly 340 at or near one of the inferior pulmonary veins and tracing or drawing a loop around the periphery of both the right and left inferior pulmonary veins such that corresponding ablation pattern is traced on the interior of the heart by ablation assembly 310. The separate lesions enclosing each of the superior and inferior pulmonary veins may then be associated or connected by placing the guiding assembly near one of the lesions and tracing or drawing a path toward the other lesion, thereby connecting both lesions.

Figure 3A:
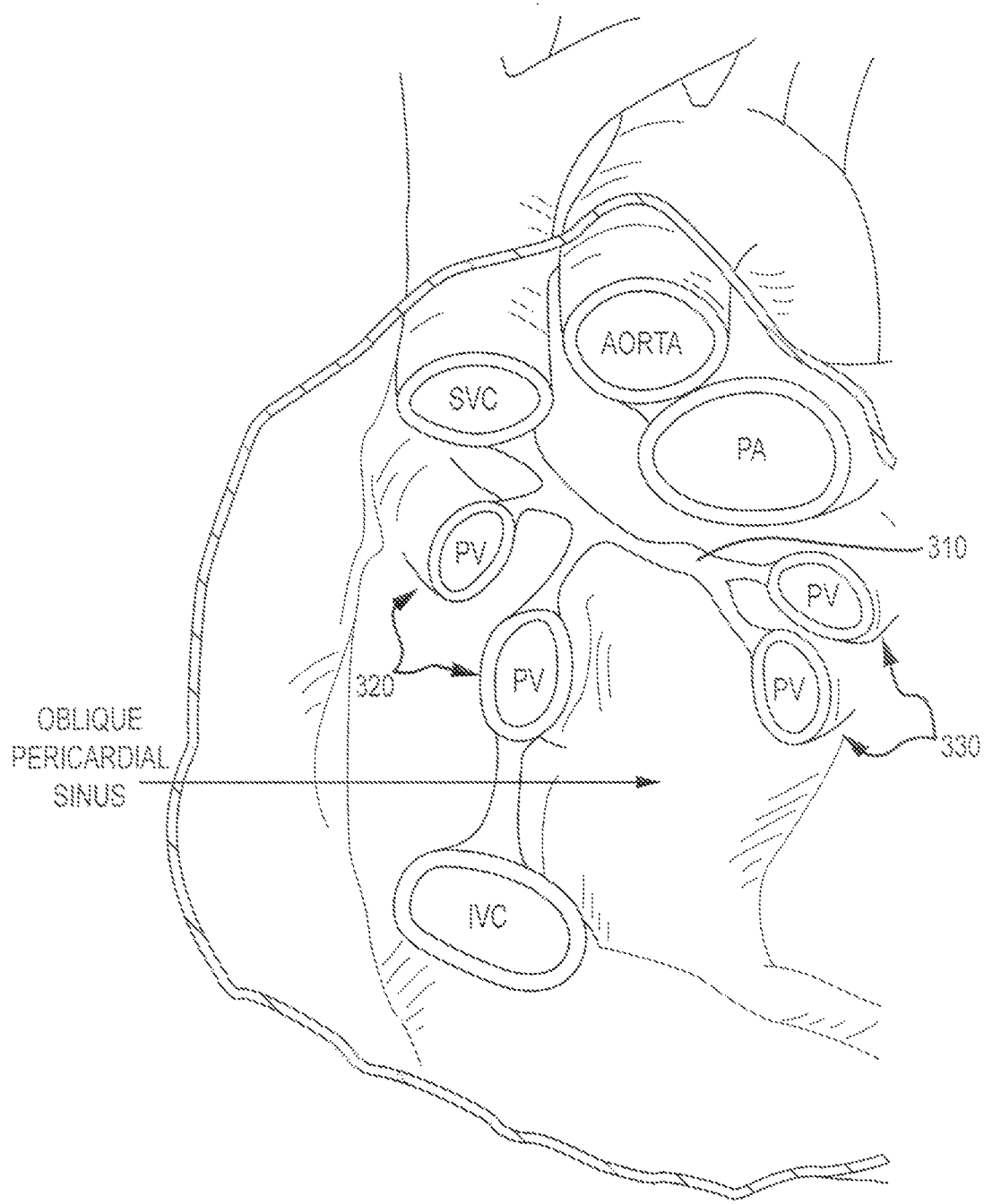
FIG. 3A illustrates aspects of patient anatomy.

A pericardial reflection is typically present between the right and left pulmonary veins. The process of ablating between the right and left pulmonary veins, for example as illustrated by lesion or ablation pattern 362, may involve a concomitant dissection of the pericardial reflection between the right and left pulmonary veins at or near the epicardium. The pericardial reflection presents a ridge or line of attachment between the right and left pulmonary veins. For example, FIG. 3A illustrates a pericardial reflection 310 between the right pericardial veins 320 and the left pericardial veins 330.

When navigating a treatment system, in some cases it may be desirable to avoid placing the system in close proximity to the circumflex artery, or to avoid generating undue temperature conditions near the circumflex artery. Endocardial techniques may be less likely to generate such temperatures as compared with bipolar or epicardial techniques. Similarly, it may be desirable to avoid placing an ablation element within the interior of a pulmonary vein. Embodiments of the present invention, including epicardial magnetic techniques, are well suited for providing techniques that involve a reduced or minimized probability of placing an ablation element within the interior of a pulmonary vein, or within the interior of the left atrial appendage orifice.

The aortic valve has three bulging components, or cusps. One cusp contains a left artery and another cusp contains a right coronary artery. A third cusp does not contain any coronaries, and is where aortic valve is transitioned and attached to the aorta. This area is also known as the fibrous trigone, a fibrous ring shared by both the aorta and the mitral valve. Embodiments of the present invention involve ablating or creating a lesion at or near the trigone. For example, a connecting lesion can be formed at the trigone on the left atrium, to a location that is near both the aortic valve and the mitral valve. Epicardial techniques are well suited for creating such lesions. With an epicardial ablation approach, using a system with an ablation element at the epicardial surface, it is possible to form a lesion to the mitral valve annulus. Such lesions can help to reduce atrial flutter.

FIG. 4 illustrates use of treatment system 400 to create a lesion substantially enclosing the pulmonary vein ostia and a lesion extending toward the mitral valve. In accordance with procedure described herein, a lesion substantially enclosing ostia of pulmonary veins, 475, 480, 485, and 490 respectively, may be created by positioning guiding assembly 440 at or near one of the pulmonary veins and tracing or drawing a loop around the periphery of the superior and inferior pulmonary veins so that corresponding ablation pattern 460 is traced on the interior of the heart and a lesion is created along the ablation pattern. In a similar manner, a lesion may be created stemming from the lesion enclosing the pulmonary veins and extending towards the mitral valve 468 by placing guiding assembly 440 at or near the lesion enclosing the pulmonary veins and tracing or drawing a path toward the mitral valve 468 that corresponds with ablation pattern 465. In some cases, a lesion extending toward mitral valve 468 may be positioned closely to the right inferior pulmonary vein and extend substantially to the mitral valve.

According to embodiments of the present invention, a treatment system can be introduced into the patient's body and placed at or near the heart tissue using any of a variety of insertion techniques. For example, methods for placing or positioning devices at, near, into, between, or among certain anatomical features within the patient's body, for example within the patient's thoracic cavity, are described in U.S. patent application Ser. Nos. 12/124,743 and 12/124,766, filed May 21, 2008, Ser. No. 12/339,331 filed Dec. 19, 2008, and 61/051,975 filed May 9, 2008. The entire disclosure of each of these references is incorporated herein by reference for all purposes. Exemplary treatment system positioning techniques may involve navigation at or near the transverse and oblique sinuses, or breaking through the pericardial reflection where pericardium attaches to heart, or passing between or around the right and left pulmonary veins, or any combination thereof. Certain approaches can entail dissection of attachments that occur near the transition between the right atrium and the left atrium.

Figure 5A:
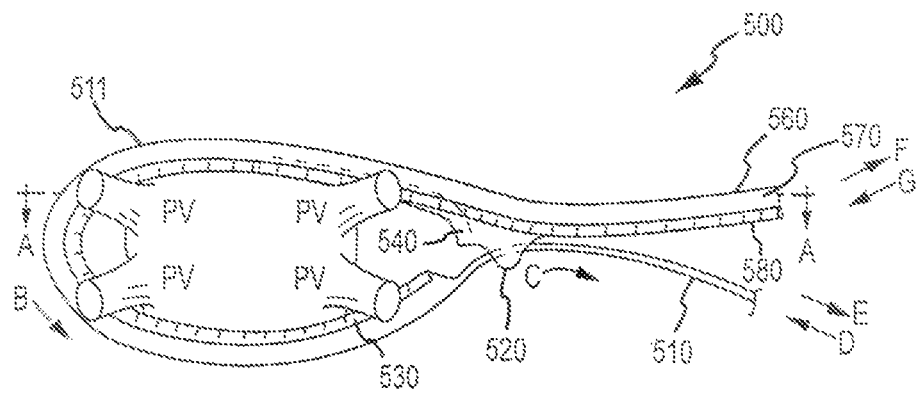
FIGS. 5A-5F illustrate aspects of ablation treatment systems and methods according to embodiments of the present invention.
Figure 5B:
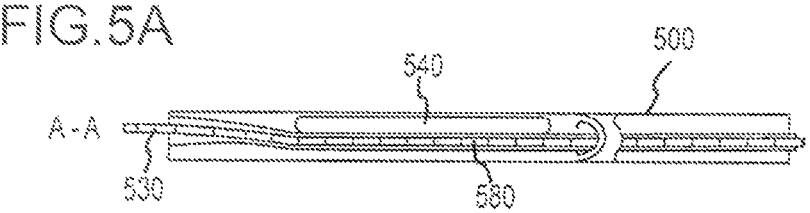
Figure 5C:
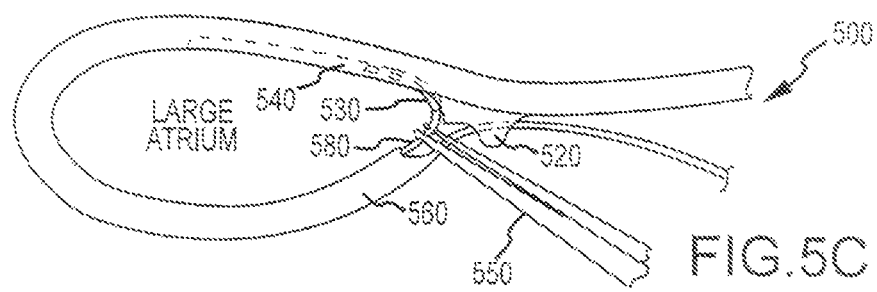
Figure 5D:
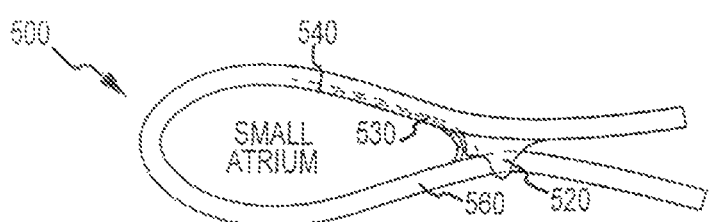

Guiding assemblies can be maneuvered about the surface of heart or cardiac tissue by guidance systems which are well suited for creating certain lesion configurations, such as box lesions. FIGS. 5A-5F depict aspects of guidance systems according to embodiments of the present invention. It is noted that similar device positioning features are described with reference to ablation systems disclosed in previously incorporated U.S. Patent Application No. 60/939,201 filed May 21, 2007, U.S. patent application Ser. Nos. 12/124,743 and 12/124,766 filed May 21, 2008. Any of the positioning or placement techniques described in these applications can be similarly used for maneuvering guiding assemblies relative to patient tissue. For example, FIG. 5A shows a guiding system 500 having a distal end 510 and a belt loop 520. Further, the guiding system includes a guiding assembly 530. Distal end 510 of system 500 is disposed through belt loop 520. FIG. 5B shows a cross-section view of a portion A-A of FIG. 5A. As depicted in FIG. 5C, guidance system 500 can be disposed about a large atria. Similarly, as depicted in FIG. 5D, guidance system 500 can be disposed about a small atria. According to FIG. 5E, guidance system 500 can have a receiving slot 540 adapted to receive guiding assembly 530. According to FIG. 5F, guidance system 500f can include an ablation element 533f.

With a more detailed reference now to FIG. 5A, guidance system 500 includes a flexible guiding member 580, an encircling mechanism or catch 520 such as a belt loop, a hook, a closable clasp, or the like, and a flexible stabilizer member or bracing 560 having a distal end 510, a proximal end 570, and a recessed receiving slot or receptacle 540. As depicted here, flexible guiding member 580 may be attached with or include a guiding assembly 530, which can include an attraction element such as a magnet. The combination of the guiding member 580 (or the guiding assembly 530) and the stabilizer member 560 can collectively be referred to as the guidance system 500. In use, an operator may treat a patient by wrapping a loop structure 511 of the guidance system 500 around one or more pulmonary veins (PV) of a patient. This may involve passing flexible bracing distal end 510 circumferentially around the tissue as indicated arrow B, and through belt loop 520 as indicated by arrow C. The operator may expand or contract guidance system 500 by manipulating the flexible stabilizer member distal end 510. Moving distal end 510 in direction D results in contraction of loop structure 511 of guidance system 500 in a cinching fashion. Moving distal end 510 in direction E results in expansion of loop structure 511 of guidance system 500. Stabilizer member 560 may be made of or include any suitable flexible material, such as a silicone, Teflon, polyurethane, polyethylene, another suitable polymer, or combination of polymers or the like.

In some embodiments of use, a surgeon or operator can pass stabilizer member distal end 510 through catch 520, and expand or contract guidance system 500 by manipulating the flexible bracing proximal end 570. Moving proximal end 570 in direction F results in contraction of loop structure 511 of guidance system 500 in a cinching fashion. Moving proximal end 570 in direction G results in expansion of loop structure 511 of guidance system 500. FIG. 5B depicts a cross-section portion A-A of guidance system 500 as shown in FIG. 5A. As shown here, receiving slot 540 is located adjacent to guiding member 580. In some cases, receiving slot 540 might be located on either side of guiding member 580. Receiving slot 540 is adapted to receive a distal section of guiding member 580 or guiding assembly 530.

As shown in FIG. 5C, a surgeon or operator can detach or separate guiding assembly 530 from stabilizer member 560 and insert portion 530 into receiving slot 540, for example by grasping and manipulating the portion 530 with a positioning device 550. In some cases, a distal portion of the stabilizer member can be inserted through catch 520. A positioning device such as a forceps or grasper can be introduced into the patient via a minimally invasive incision or port. For example, a stab device having a cylindrical opening can present a cutting point that expands as it is introduced into the patient's tissue. In some cases, a port may include a valve. Optionally, a fluid or gas such a carbon dioxide can be introduced via the port, and can effectively displace or push away lung tissue, thereby providing an operating space within the patient's chest. Instruments, including imaging devices, may be inserted and removed via an incision or port. Positioning device 550 may be used by the operator to detach guiding assembly 530 from flexible bracing 560 and to insert the detached section of section 530 into receiving slot 540 so that guiding member 580 approximately encircles tissue of a heart.

In some cases, bracing 560 can be aligned such that the operator can simply advance guiding member 580 or guiding assembly 530 along bracing 560, without additional assistance from positioning device 550, such that the guiding assembly tracks along the bracing, extending from a distal portion of the bracing and returning to a more proximal portion of the bracing.

As depicted in FIG. 5A, for example, guidance system 500 can be configured so as to substantially enclose or encircle all four pulmonary veins (PV). By translating guiding assembly 530 along stabilizer member 560, the operator can create a box lesion around the pulmonary veins with an ablation element that is disposed within the interior of the heart. Hence, an operator can administer ablative energy through an ablation member to produce a circular or closed ablation pattern or lesion on the patient tissue. The ablation element can be used to produce any of a variety of circular, elliptical, or closed ablation patterns or lesions from the interior of the large atria. As shown in FIG. 5D, guidance system 500 may be used to help produce an ablation pattern or lesion on a small atria. Because the atria is smaller, a longer section of flexible stabilizer member 560 may be moved though catch 520 in order to snugly fit the guiding assembly around the atria. This may involve a longer section of distal guiding assembly 530 being inserted into receiving slot 540. By administering ablative energy through an ablation system disposed within the interior of the heart, an operator can use guidance system 500 to help produce any of a variety of circular, elliptical, or closed ablation patterns or lesion from the interior of the small atria.

Figure 5E:
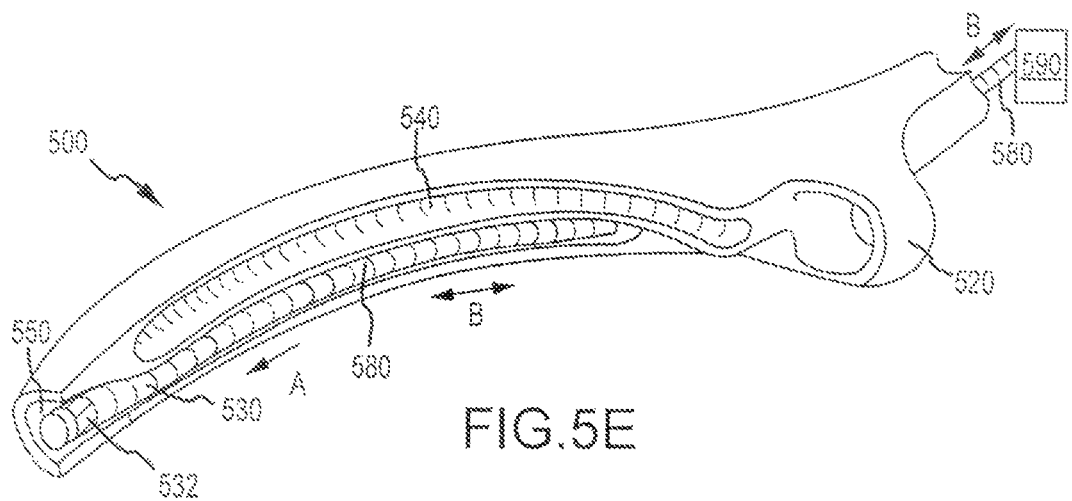

FIG. 5E provides a partial view of guidance system 500. Catch 520 is shown without the distal end of flexible bracing 510 inserted therein. In this embodiment, guiding member section 580 is partial recessed or disposed within a receptacle or slot 550 of flexible bracing 560. Receiving slot 540 is adapted to receive a distal section of guiding assembly 530 after the guiding assembly is advanced distally along slot 550 in the direction indicated by arrow A. As depicted here, a distal portion of guiding assembly 530 can include an attraction element 532 such as a magnet. Guiding assembly 530 can be advanced distally or retracted proximally as indicated by arrow B. In some embodiments, such translational motion can be effected with any of a variety of motorized or mechanized elements, such as gears, drives, rack and pinion assemblies, worm gear assemblies, and the like. As depicted in FIG. 5E, guiding assembly 530 can be coupled with a drive mechanism 590, which provides translational movement to guiding assembly 530 or guiding member 580. Guiding assembly 530 can present any of a variety of attraction element configurations. In some cases, an attraction element may include a flexible material, so as to facilitate good contact between the guiding assembly and the surface contours of the patient tissue or organ.

Figure 5F:
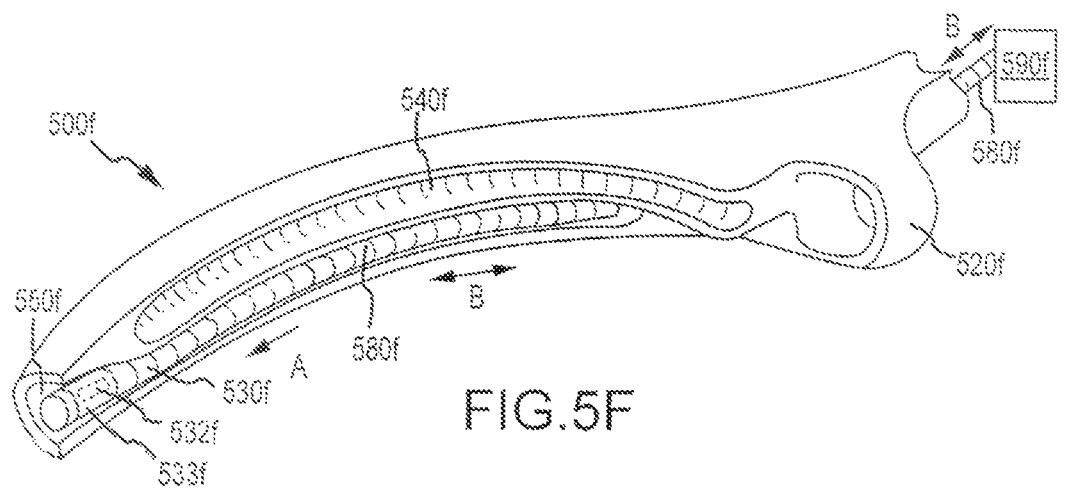

FIG. 5F provides a partial view of guidance or ablation system 500f. Catch 520f is shown without the distal end of flexible bracing 510f inserted therein. In this embodiment, guiding member section 580f is partial recessed or disposed within a receptacle or slot 550f of flexible bracing 560f. Receiving slot 540f is adapted to receive a distal section of guiding assembly 530f after the guiding assembly is advanced distally along slot 550f in the direction indicated by arrow A. As depicted here, a distal portion of guiding assembly 530f can include an attraction element 532f such as a magnet, and an ablation element 533f such as an RF electrode. Guiding assembly 530f can be advanced distally or retracted proximally as indicated by arrow B. In some embodiments, such translational motion can be effected with any of a variety of motorized or mechanized elements, such as gears, drives, rack and pinion assemblies, worm gear assemblies, and the like. As depicted in FIG. 5F, guiding assembly 530f can be coupled with a drive mechanism 590f, which provides translational movement to guiding assembly 530f or guiding member 580f. Guiding assembly 530f can present any of a variety of attraction element configurations. In some cases, an attraction element may include a flexible material, so as to facilitate good contact between the guiding assembly and the surface contours of the patient tissue or organ.

Figure 6A:
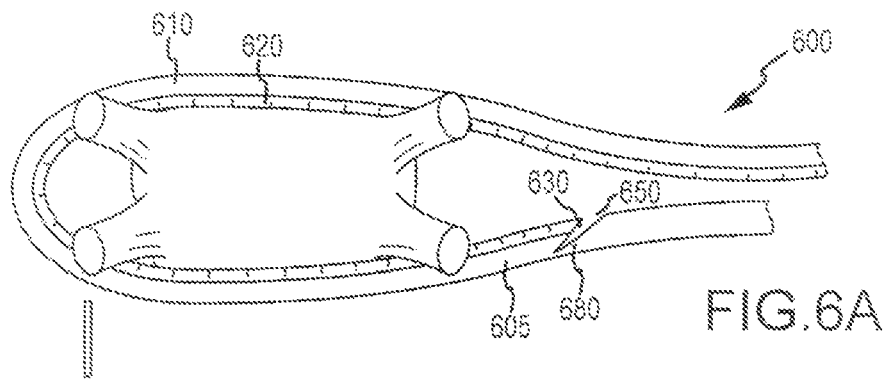
FIGS. 6A-6E illustrate aspects of ablation treatment systems and methods according to embodiments of the present invention.
Figure 6B:
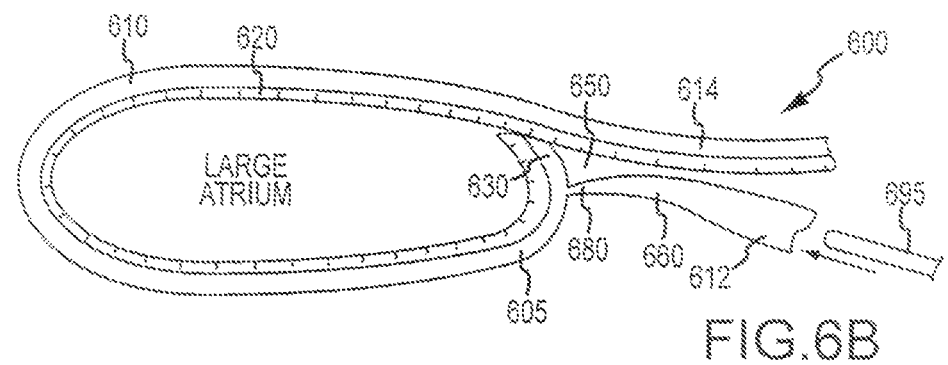
Figure 6C:
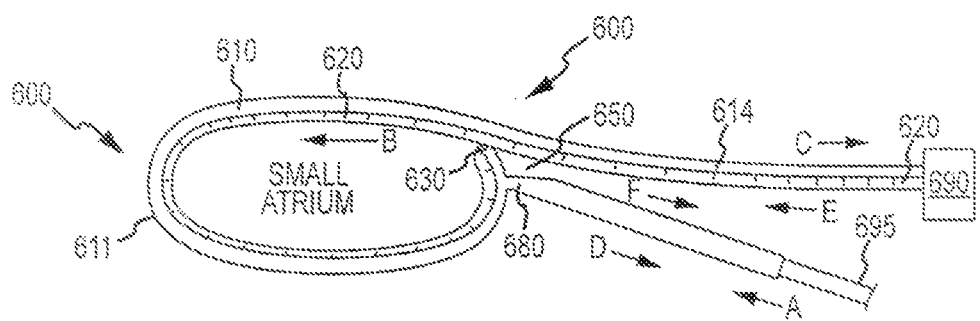

Referring now to FIG. 6A, in some embodiments an guidance system 600 includes a flexible device which includes an encircling mechanism 605 having a breakaway tip 630, a slit 650, and a living hinge 680. Guidance system 600 also includes a guiding member 620 in operative association with a stabilizer member 610. The stabilizer member can operate as a raceway or track, and guiding member 620 can translate in a forward or backward direction within the raceway. The raceway can house an ablation element or a navigation or guiding element. As shown in FIG. 6B, guidance system 600 can be extended around a large atrium of a patient. In use, a surgeon can insert a stiffening probe 695 into a distal end 612 of stabilizer member 610. By manipulating distal end 612 of stabilizer member 610, or by adjusting proximal end 614 of stabilizer member 610 relative to encircling mechanism 605, an operator can activate hinge 680 and move breakaway tip 630 toward the atrium. This pushing action causes breakaway tip 630 to move away from a portion 660 of the stabilizer member that is located on the opposing side of slit 650. Hence, breakaway tip 630 can act as an extension of the raceway for a guiding member, or for an ablation member, allowing such a guiding member or ablation member to travel in a circular path around the heart tissue. In some cases, slit 650 extends about half way through a cross section of the stabilizer member. In a manner similar to that described above with reference to FIGS. 5A-5F, an operator can transmit ablative energy through an ablation member disposed within the heart chamber, so as to produce an approximately circular, elliptical, or closed ablation pattern or lesion. As shown in FIG. 6C, an operator can use guidance system 600 to help apply ablative energy to a small atrium, in a similar fashion. Stiffening probe 695 can be pushed farther toward the heart, in the direction indicated by arrow A, which can cause the expansion of a wider angle defined by slit 650, as hinge 680 opens further and breakaway tip 630 moves more distally along guiding member 620, as indicated by arrow B. Hence, breakaway tip 630 can move closer to the atrium, and guiding member 620 can snugly fit against the atrium. In some cases, it may be desirable to move proximal end 614 of the stabilizer member in the direction indicated by arrow C, which can also effectively move breakaway tip 630 more distally along guiding member 620, as indicated by arrow B. Optionally, the surgeon or operator can move distal portion 612 in the direction indicated by arrow D, or proximal portion 614 in the direction indicated by arrow E, so as to move the breakaway tip more proximally along the guiding member, as indicated by arrow F. In this way, by manipulating aspects of the system such as the distal end or the proximal end of a stabilizer member, an operator can adjust the size of a loop structure 611 provided by the guidance system. In some instances, the guiding member may be adjusted to contact epicardial tissue directly adjacent to the base or ostia of one or more pulmonary veins. In some instances, the ablation member may be adjusted so that a gap exists between the ablation member and the pulmonary veins.

Figure 6D:
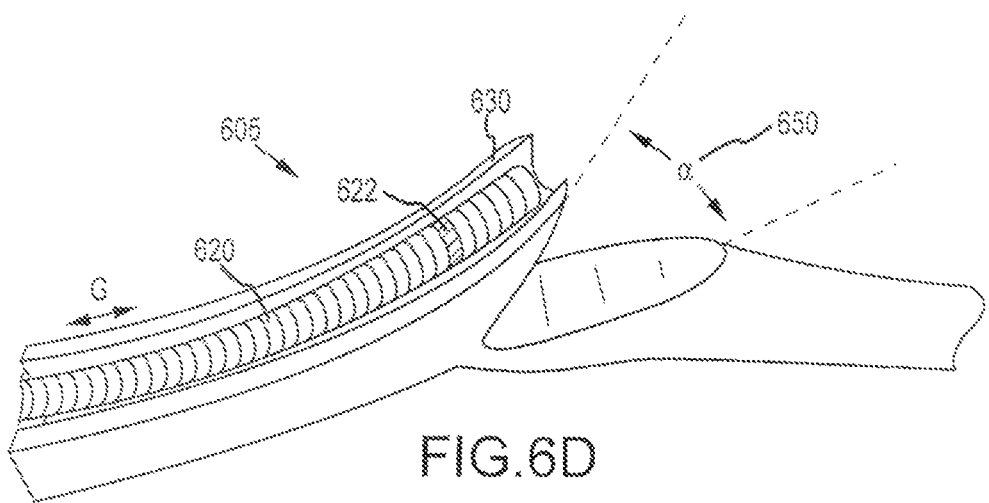
Figure 6E:
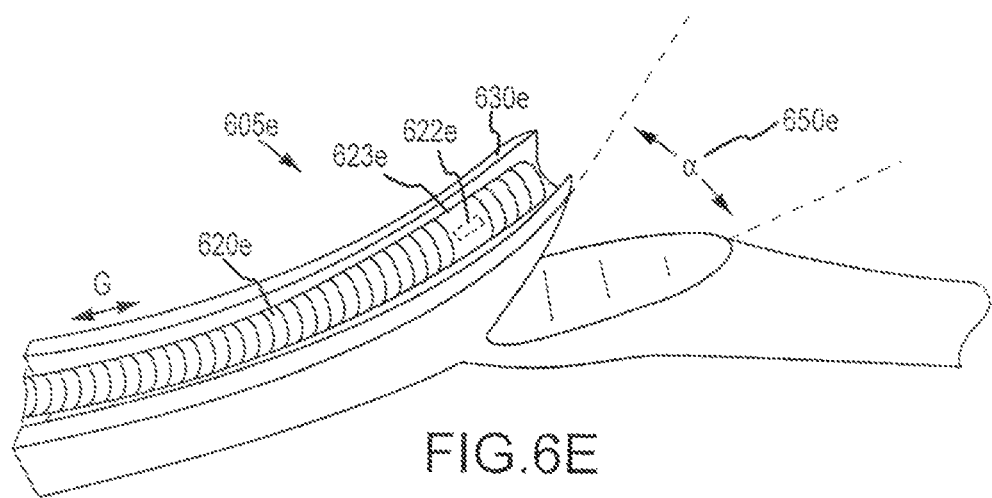

FIG. 6D provides a close-up view of encircling mechanism 605 of the ablation system, which includes breakaway tip 630, slit 650, and living hinge 680. In some embodiments, guiding member 620 can extend to the distal end or nearly to the distal end of breakaway tip 630. By manipulating aspects of the system, such the distal end or the proximal end of a guiding assembly, an operator can adjust an angle α of defined by slit 650. Hence, it is possible to conform the guiding member with a contour presented by a patient tissue. When the guiding member is placed at or near the tissue, ablative energy can be transmitted through an ablation member disposed on the other side of the tissue, thus ablating at least a portion of the tissue to form one or more lesions. As depicted in FIG. 6D, guiding assembly 620 may include an attraction element 622 such as a magnet. Guiding assembly 620 may be advanced distally or retracted proximally as indicated by arrow G. In some embodiments, such translational motion can be effected with any of a variety of motorized or mechanized elements, such as gears, drives, rack and pinion assemblies, worm gear assemblies, and the like. For example, as depicted in FIG. 6C, guiding assembly 620 can be coupled with a drive mechanism 690. FIG. 6E illustrates a guiding assembly 620e according to embodiments of the present invention. The guiding assembly includes an attraction element 622e such as a magnet, and an ablation element 623e such as an RF electrode. Guiding assembly 620e may be advanced distally or retracted proximally as indicated by arrow G. In some embodiments, such translational motion can be effected with any of a variety of motorized or mechanized elements, such as gears, drives, rack and pinion assemblies, worm gear assemblies, and the like.

With reference to FIGS. 5A-5F and 6A-6E, for example, a guiding assembly or catheter with a magnetic tip can be inserted into or through the stabilizer member, or the guiding assembly can be otherwise constrained to be captured within or translated along one or more elements of the guidance system. The guiding assembly, with the attraction elements, can be advanced or withdrawn either manually or removably connected to a motorized drive shaft that advances or withdraws the guiding assembly automatically at a predetermined rate. In some embodiments, RF power to an endocardial ablation element can be temperature feedback controlled to maintain a predetermined temperature set point, for example in the range of 50° C. to 70° C. Alternatively, RF power applied to the endocardial ablation device could be held constant and the translation rate can be feedback controlled to maintain the temperature of the endocardial ablation device at a predefined temperature, for example 60° C. In this translation mode, the ablation device can be driven over a particular point on the endocardium one or more times. One way to create a transmural ablation pattern efficiently is to return to a given spot every 5-15 seconds, since thermal conduction times can be relatively slow, whereas localized tissue heating tends to be at least 10-fold faster than the times required for heat to conduct from hotter tissues to cooler spots. The stabilizer member bracing, or epicardial tubular guide tube, can be made from a material with very low magnetic susceptibility, for example a biocompatible plastic material. Hence, components of the system can be selected so as not to interfere with the attractive or magnetic properties of the attraction elements. Exemplary materials may include polyurethane or Teflon. In some cases, the tube diameter can be within a range from about 3 mm to about 6 mm, and the wall thickness can be about 1 mm or less, so as to enable adequate magnetic attractive force between the endocardial magnetic element and the moveable magnetic catheter tip contained within the guide tube.

The embodiments depicted in FIGS. 5A-5F and 6A-6E are well suited for maintaining an attraction element such as a magnet close to the surface of the heart. Proximity between attraction elements is often desirable. For example, magnetic field strength can diminish as a function of the distance between magnets. In some embodiments, an attraction element is maintained or housed within a thin tubing or member, which can hold the attraction element in place. Optionally, this housing member can be about 0.5 mm or less in thickness. The housing member or membrane can include a biocompatible material, such as Teflon, polyurethane, or another plastic.

In some cases, the guiding assembly or introducer system can be used to move an attraction element. In some cases, the guiding assembly can be used to move an assembly that includes an attraction element, an electrode or ablation element, or a temperature sensor, or any combination thereof. Attraction elements can include devices such as magnets. For example, a magnetic member may include a combination of neodymium, iron, and boron. In some cases, a magnetic member may be nickel plated.

Optionally, the internal diameter of the tubular guide can be about 0.5 mm larger than the outer diameter of the moveable magnetic catheter to enable free and easy translation of the magnetic tip within the guide tube. Hence, embodiments of the present invention encompass systems that include a tube structure that can be routed around certain structures of the epicardium in specific formations. A tube structure can contain or house a motorized magnet within it such that the moving magnet within the tube moves from one end of the tube toward another following the anatomical path of which the tube was placed while moving a magnetically attracted catheter inside the heart along with it.

In some embodiments, guiding assemblies can be positioned or maneuvered relative to patient tissue using introducer techniques such as those described in previously incorporated U.S. Patent Application No. 61/015,472 filed Dec. 20, 2007.

Embodiments of the present invention encompass techniques for controlling temperature, and for controlling power based on temperature sensing. Examples of such approaches are described in U.S. Pat. No. 6,245,065, which discusses temperature control of ablation. The entire contents of this patent are incorporated herein by reference.

Figure 7:
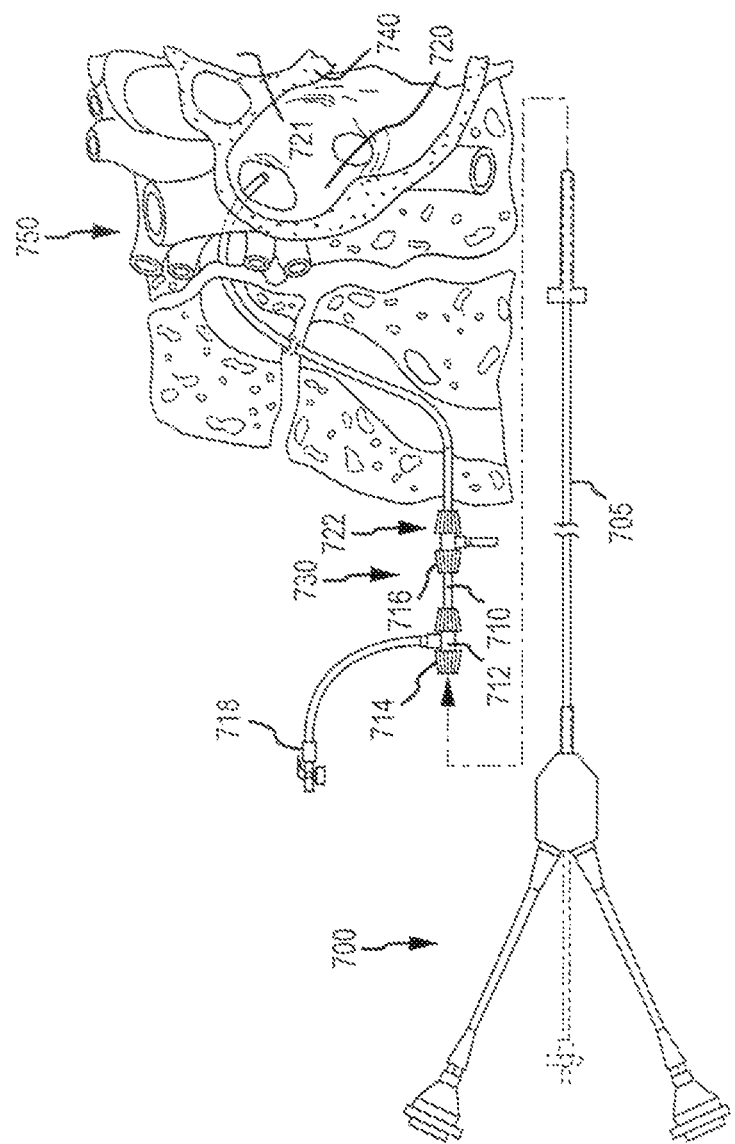
FIG. 7 illustrates aspects of ablation treatment systems and methods according to embodiments of the present invention.

Embodiments of the present invention encompass techniques for placing ablation assemblies or guiding assemblies into chambers of the heart. FIGS. 7, 8A, 8B, and 9 illustrate how an endocardial magnetic ablation element can be advanced into the left atrium. As depicted in FIG. 7, a steerable catheter 705 can be used to guide an outer sheath 710 into a desired position within the patient's heart 750. The outer guide sheath 710 includes an interior bore that receives the steerable catheter body. The physician can slide the outer guide sheath 710 along the steerable catheter body. A handle 712 of the outer sheath 710 may include a conventional hemostatic valve 714 that blocks the outflow of blood and other fluids. The valve 714 may take the form of a resilient slotted membrane or a manually operated shutter valve arrangement, for example. Valves 714 and 716 can provide an effective hemostatic system, and thus allow performance of a procedure in a clean and relatively bloodless manner. In use, the steerable catheter body enters the bore of the guide sheath 710 through the valve 714. The handle 712 of the outer sheath 710 also may include a flushing port 718 for the introduction of an anticoagulant or saline into the interior bore. The physician can advance the catheter body and the outer guide sheath 710 together through the femoral vein. The physician may retain the sheath handle 712 near the catheter handle to keep the catheter tip outside the distal end of the outer sheath 710. In this way, the physician can operate a steering lever to remotely point and steer the distal end of the catheter body while jointly advancing the catheter body through the femoral vein. The physician can observe the progress of the catheter body using fluoroscopic or ultrasound imaging, or the like. The outer sheath 710 can include a radio-opaque compound, such as barium, for this purpose. The physician can locate the distal end of the catheter body in the right atrium 720, and the outer sheath handle 712 can be slid forward along the catheter body, away from the handle and toward the introducer 722. The catheter body can direct the guide sheath 710 fully into the right atrium 720. Holding the handle 712 of the outer sheath 710, the physician can withdraw the steerable catheter body from the outer guide sheath 710. Thus, the delivery system 730 can be deployed in the condition generally shown in FIG. 7.

The system 730 creates a passageway that leads through the femoral vein directly into the right atrium 720. The delivery system 730 provides this access without an invasive open heart surgical procedure. Alternatively, the outer guide sheath 710 can itself be preshaped with a memory. The memory may assume a prescribed curvature for access to the right or left atrium 720 or 721 through venous access, without need for a steerable catheter. To assist passage through the atrial septum 740, the delivery system 730 may include a transeptal sheath assembly. The delivery system 730 can guide the sheath assembly into the right atrium 720 and through the atrial septum 740 to open access to the left atrium 721. The delivery system 730 further includes an ablation probe to carry a selected ablating element.

Figure 8A:
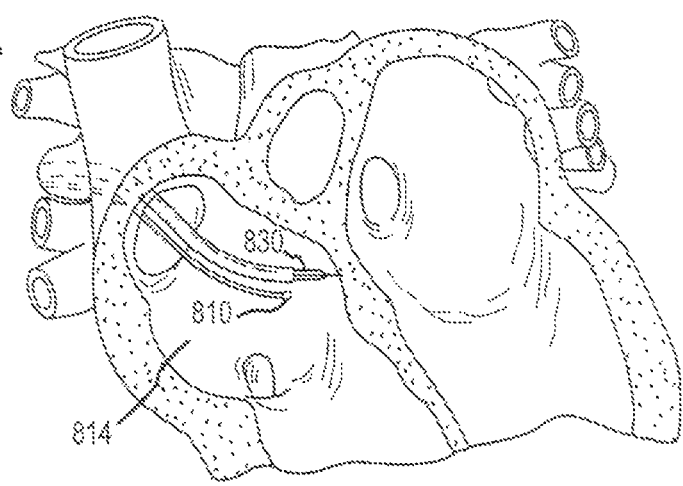
FIGS. 8A-8B illustrate aspects of ablation treatment systems and methods according to embodiments of the present invention.
Figure 8B:
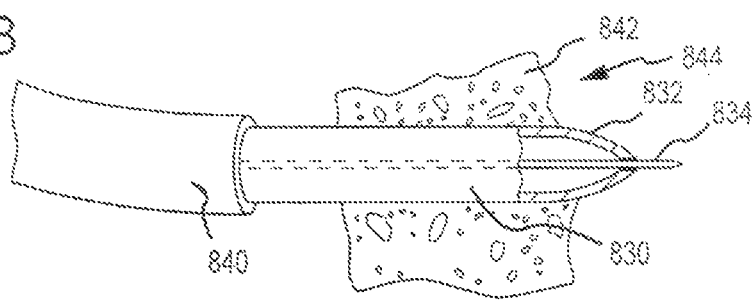

As depicted in FIG. 8A, a physician may deploy a visualization device 810, such as an ultrasonic viewing probe, through the femoral vein into the right atrium 814, either within or outside a guide sheath. Alternatively, fluoroscopy or other visualization modalities could be used. The physician can operate the visualization device to observe other system elements disposed within the heart. As shown in FIG. 8B, the physician or operator can advance the transeptal sheath assembly 830 through the guide sheath 840 into the atrial septum 842. The viewing probe can be used to monitor the position of the guide sheath 840 and the advancement of the transeptal sheath assembly 830 toward the atrial septum 842. The transeptal sheath assembly 830 includes a cutting edge or dilator 832 that carries a sharpened lead wire 834. As the physician advances the transeptal sheath assembly 830, the lead wire 834 forms an initial opening in the septum 842. The dilator 832 enters this opening, enlarging it and punching through to the left atrium 844. This transeptal approach is well suited for left atrium access procedures. The physician can slide the guide sheath 840 along the transeptal sheath assembly 830 and into the left atrium 844. The physician can then withdraw the transeptal sheath assembly 830 from the guide sheath 840, such that the guide sheath 840 forms a path through the femoral vein and right atrium into the left atrium 844.

Figure 9:
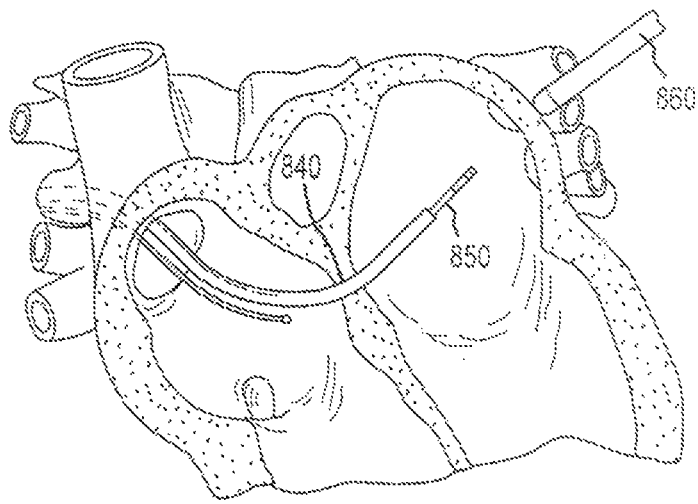
FIG. 9 illustrates aspects of ablation treatment systems and methods according to embodiments of the present invention.

As depicted in FIG. 9, the physician or operator can introduce an ablation assembly 850 through guide sheath guide sheath 840. Thus, the ablation assembly 850 can be placed inside of the heart and adjacent to the endocardial tissue. A guiding assembly 860 can be placed outside of the heart. The operator can use magnetic attraction present between a guiding assembly magnet and an ablation assembly magnet to help guide the ablation assembly so as to form an ablation or desired pattern of lesions on the endocardial tissue of the patient's heart with an ablation element of the ablation assembly. Upon establishing the desired lesion pattern, the physician can withdraw the ablation assembly 850 from the guide sheath 840, and then withdraw the guide sheath 840 from the heart and femoral vein. Relatedly, it is understood that transeptal introduction can be achieved by inserting an introducer or sheath with an internal dilator through the femoral or jugular vein and into the interior of the right atrium. Once in the right atrium, a long hollow needle with a preformed curve and a sharpened distal tip can be introduced through the dilator and can be forcibly inserted through the fossa ovalis. A radiopaque contrast material can be injected through the needle to ensure the needle is in the left atrium as opposed to being in the pericardial space, aorta, or other undesired location. Once the position of the needle in the left atrium is confirmed, the dilator and sheath can be advanced over the needle and into the left atrium. Then, the needle and dilator can be removed leaving the sheath/introducer as an access point to the left atrium. An endocardial catheter containing one or more ablation elements and magnetic elements can be inserted into the introducer and the catheter can be advanced into the left atrial chamber. The tip of the catheter can be advanced and steered to the approximate site within the left atrium that is to be ablated. Any of a variety of steering techniques can be used to advance the endocardial ablation catheter so as to bring the magnet of the ablation catheter into sufficient proximity with the magnet of the guiding assembly, such that a magnetic attraction is established between the endocardial ablation catheter and the guiding assembly. Suitable steering techniques for this process can be found in U.S. Pat. Nos. 5,820,591 and 7,115,122, the content of which are incorporated herein by reference.

According to some embodiments, a non-circumferential balloon or structure can be placed over an ablation catheter section. For example, as depicted in FIG. 10A, an ablation assembly 1000 can include a catheter body 1010, an attraction element 1020 such as a magnet, an ablation element 1030 such as an electrode, and a support structure 1040 such as a non-circumferential balloon. The ablation electrode 1030 is placed on the catheter body 1010 at a location 1012 where the balloon 1040 does not extend circumferentially about the catheter body. Balloon 1040 does extend circumferentially about the catheter body at a location 1014 distal to the ablation element, and at a location 1016 proximal to the ablation element. Hence, the support structure 1040 provides a cavity or space 1018 between the electrode 1030 and the surface of a patient tissue 1050 when the ablation assembly 1000 is disposed at or near the patient tissue 1050.

FIG. 10B shows a schematic illustration of an RF ablation catheter system including an electrode structure constructed in accordance with an embodiment of the present invention. RF ablation catheter 1000*b* includes a microporous electrode body 1120*b*. The catheter 1000*b* may be connected to a RF generator 1200*b* such as that described in Jackson et al., U.S. Pat. No. 5,383,874, the specification of which is fully and expressly incorporated herein by reference. The RF generator 1200*b* provides the catheter 1000*b* with a source of RF ablation energy. Thus, when operated, the RF generator 1200*b* allows the physician to ablate tissue such as heart tissue in a controlled manner, resulting in a tissue lesion with the desired characteristics. The catheter 1000*b* may also be connected to a motor drive unit 1300*b* and an ultrasonic (or other imaging) signal processor 1400*b*, which when operated, allows the physician to obtain images of the target tissue site, for example during and subsequent to the ablation process. The catheter 1000*b* can be functionally divided into four regions: the operative distal catheter region 1102*b*, a deflectable catheter region 1104*b*, a main catheter region 1106*b*, and an interfacing proximal catheter region 1107*b*. The microporous electrode body 1120*b* of the distal catheter region 1102*b* represents the active component that provides the ablative capability to the catheter 1000*b*. The deflectable catheter region 1104*b* provides steering capability to the catheter 1000*b*, and particularly, provides an efficient and effective means for manipulating the distal catheter region 1102*b*. The main catheter region 1106*b* provides the catheter 1000*b* with a useful length to deliver the distal catheter region 1102*b* from the insertion point of the patient (for example, the femoral vein or artery) to the targeted tissue site. Lastly, the proximal catheter region 1107*b*, which includes a handle assembly 1132*b* and a proximal adapter 1174*b*, provides interfacing capability between the catheter 1000*b* and other instruments such as the RF generator 1200*b*, motor drive unit 1300*b*, and signal processor 1400*b*, as well as a means for introducing and removing fluids into and out of the catheter 1000*b*.

FIG. 10C shows a partial side-elevational view of an embodiment of the catheter of FIG. 10B, depicting the operative distal region, deflectable region, and main region of the catheter. The catheter includes a catheter body 1108*c* that carries a differing number of functional lumens and may have varying flexibility along its length. In this regard, the catheter body 1108*c* is composed of several extruded tubular elements affixed together in an axial arrangement. In particular, the catheter body 1108*c* may include first and second tubular elements 1110*c*, 1112*c*, which form, in conjunction, the structure of the distal catheter region 1102*c*; a third tubular element 1114*c*, which forms the structure of the deflectable catheter region 1104*c*; and a fourth tubular element 1116*c*, which forms the structure of the main catheter region 1106*c*. It should be noted, however, that the catheter body 1108*c* may include any number of tubular elements to provide the desired functionality to the catheter. The tubular elements 1110*c*, 1112*c*, 1114*c*, and 1116*c* may be composed of a flexible and biocompatible material. In some cases, the second, third, and fourth tubular elements 1112*c*, 1114*c*, and 1116*c* may be composed of a non-conductive thermoplastic elastomer such as polyurethane. Optionally, if ultrasound imaging is used, the first tubular element 1110*c* can be composed of a more ultrasound transparent material such as polyethylene. The tubular elements 1112*c*, 1114*c* and 1116*c* can be suitably bonded together, for example by means such as adhesive or thermal bonding to integrally form the catheter body 1108*c*. Additionally, heat shrink tubing (not shown) can be shrunk over the catheter body 1108*c* to provide a more integral catheter structure. The catheter body 1108*c* can be variously sized, assuming the selected size allows the catheter body 1108*c* to be routed through the vasculature of the patient to the targeted tissue site. By way of a non-limiting example, a 9 F catheter body 1108*c* having a length of 100 cm can allow the catheter distal region 1102*c* to be delivered to the interior of the heart via the femoral vein or artery.

A catheter distal region can carry an ablation assembly, which includes a expandable-collapsible electrode body or structure and an actuating electrode, and for example, an electrode ring. The electrode body can be suitably mounted to the catheter body such that an interior region of the electrode body is in communication with substantially the entire exterior surface of a first tubular element, and at least a portion of the exterior surface of a second tubular element. The geometry of the electrode body may be altered between a collapsed geometry and an enlarged, expanded geometry. An inflation medium under pressure can be used to fill the interior region, and thus, inflate and maintain the electrode body in the expanded geometry. The inflation medium can be conveyed to and from the interior region of the electrode body via an inflation lumen formed through the catheter body, for example through second, third and fourth tubular elements. The inflation lumen can be in fluid communication with the interior region of the electrode body via an infusion hole formed through the wall of the catheter body, and optionally, the wall of the second tubular element. With reference further to FIG. 10B, the inflation lumen can terminate proximally in the handle assembly 1132*b*, and optionally within a handle 1133*b* of the handle assembly 1132*b*. The handle assembly 1132*b* can further include an inflation port 1134*b*, which can be in fluid communication with the inflation lumen within the handle 1133*b*. Thus, inflation medium can be introduced into, or removed from, the inflation port, providing a convenient means of selectively inflating and deflating the electrode body.

Figure 11:
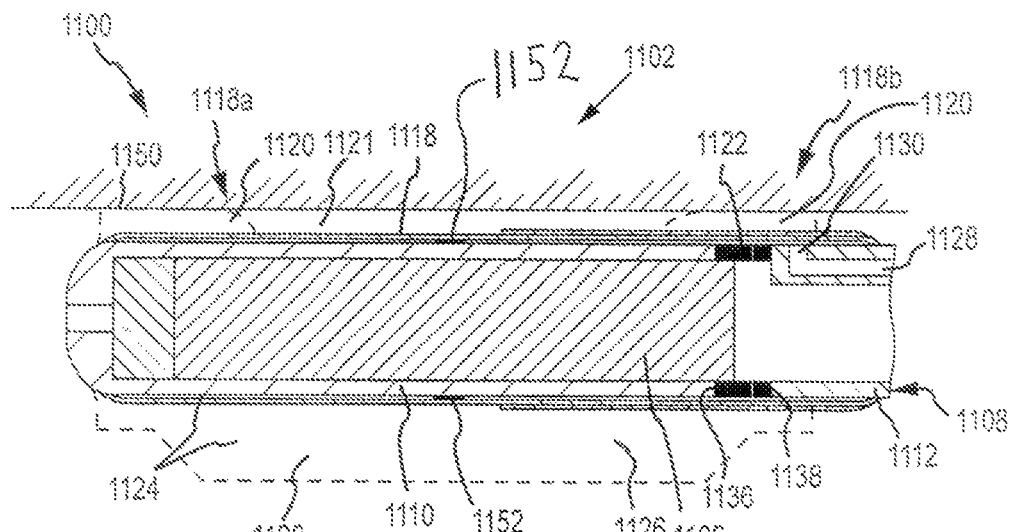
FIG. 11 illustrates aspects of ablation treatment systems and methods according to embodiments of the present invention.
Figure 12:
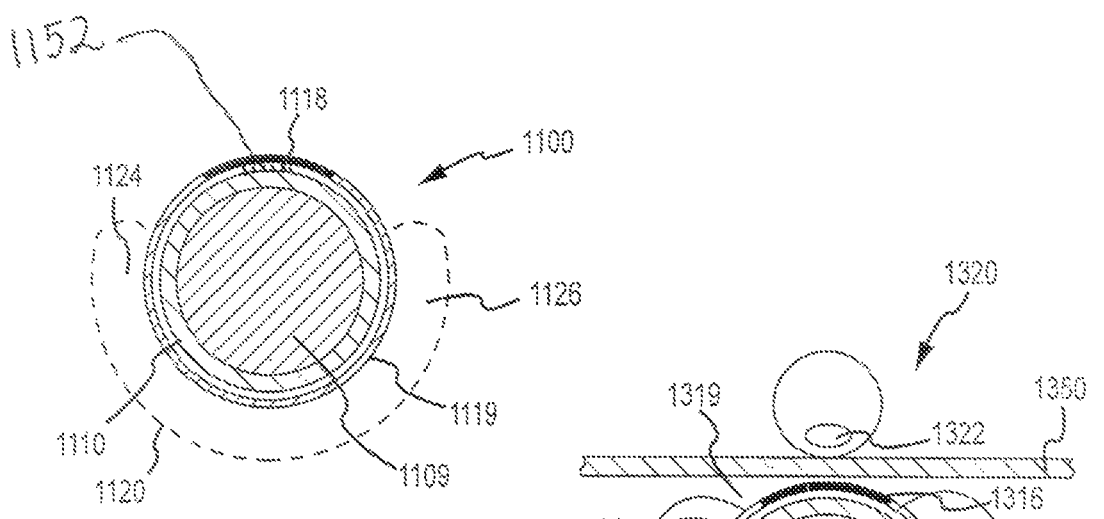
FIG. 12 illustrates aspects of ablation treatment systems and methods according to embodiments of the present invention.

FIGS. 11 and 12 provide illustrations of an exemplary ablation assembly 1100 according to embodiments of the present invention. The catheter distal region 1102 carries an ablation element 1118 and an expandable-collapsible body or structure 1120 that is mounted to the catheter body 1108. A magnet 1109 or attraction element is coupled with or disposed within catheter body 1108. The geometry of the expandable body 1120 may be altered between a collapsed geometry and an enlarged, expanded geometry (represented by broken line). In the illustrated embodiment, an inflation medium 1126 under pressure is used to fill the interior region 1124, and thus, inflate and maintain the expandable body 1120 in the expanded geometry. The inflation medium 1126 is conveyed to and from the interior region 1124 of the expandable body 1120 via an inflation lumen 1128 formed through the catheter body 1108. The inflation lumen 1128 is in fluid communication with the interior region 1124 of the expandable body 1120 via an infusion hole 1130 formed through the wall of the catheter body 1108, and specifically, the wall of a tubular element 1112.

An electrode ring 1122 is located between the first tubular element 1110 and the second tubular element 1112. In particular, a proximal edge 1136 of the first tubular element 1110 and a distal edge 1138 of the second tubular element 1112 are affixed to the opposite edges of the electrode ring 1122 by suitable means such as adhesive or thermal bonding, providing an integral connection between the first tubular element 1110 and the second tubular element 1112. The electrode ring 1122 provides RF energy to the ablation element 1118. In this regard, the electrode ring 1122 is composed of a material having both a relatively high electrical conductivity and a relatively high thermal conductivity, e.g., stainless steel, gold, platinum, or platinum/iridium. To facilitate control of the RF energy delivery, the catheter 1100 may include one or more temperature sensing elements 1152.

As shown here, at least a portion of the ablation electrode 1118 can be placed along the catheter body 1108 at a location where the balloon 1120 does not extend circumferentially about the catheter body. Balloon 1120 does extend circumferentially about the catheter body at a location 1118a distal to the ablation element, and at a location 1118b proximal to the ablation element. Hence, the support structure 1120 provides a cavity or space 1121 between the electrode 1118 and the surface of a patient tissue 1150 when the ablation assembly 1100 is disposed at or near the patient tissue 1050. In some case, ablation electrode 1118 may be mounted on an ablation electrode support 1119. Ablation assemblies may also incorporate various additional features such as those described in U.S. Pat. No. 6,893,437, the content of which is incorporated herein by reference for all purposes.

Figure 10:
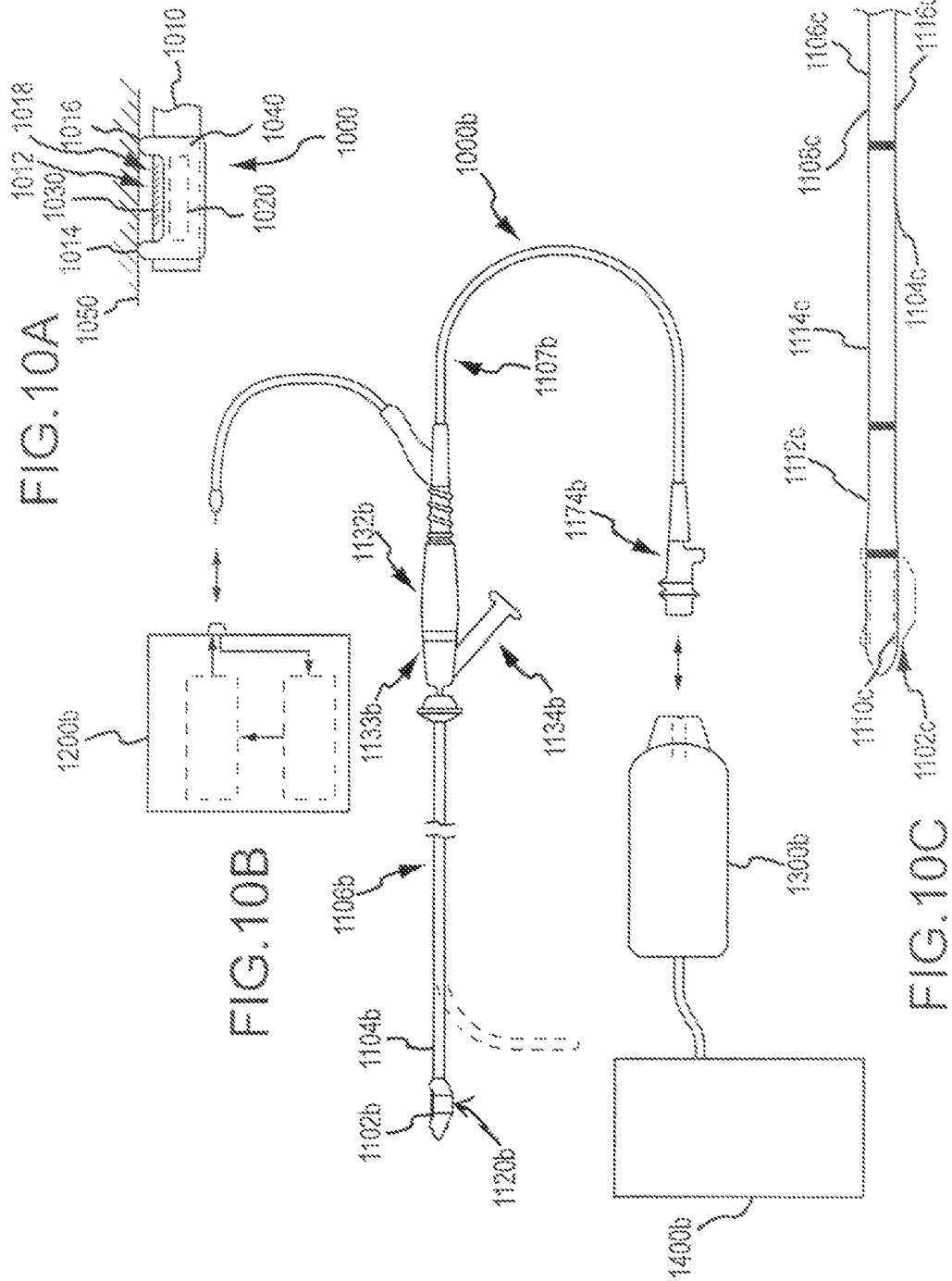
FIGS. 10A-10C illustrate aspects of ablation treatment systems and methods according to embodiments of the present invention.

With many currently available energy-based ablation devices, the applied energy heats not only the targeted heart tissue, but also blood. Such uncontrolled heating of blood can coagulate blood or even create a char-like residue that results in emboli to the brain and other vital organs. In embodiments such as those described herein with reference to FIGS. 10 to 12, for example, an endocardial ablation structure or technique can limit the amount of blood so heated and provides a more controlled lesion-making process. FIG. 10 depicts a partial side-elevation view of such a catheter, including an overview of the construction of the distal portion of the catheter. FIG. 11 provides a longitudinal cross-sectional view of the distal region of such a catheter. FIG. 12 illustrates a cross-sectional view of the distal section of such a catheter, taken at the midpoint of the balloon structure.

Figure 13:
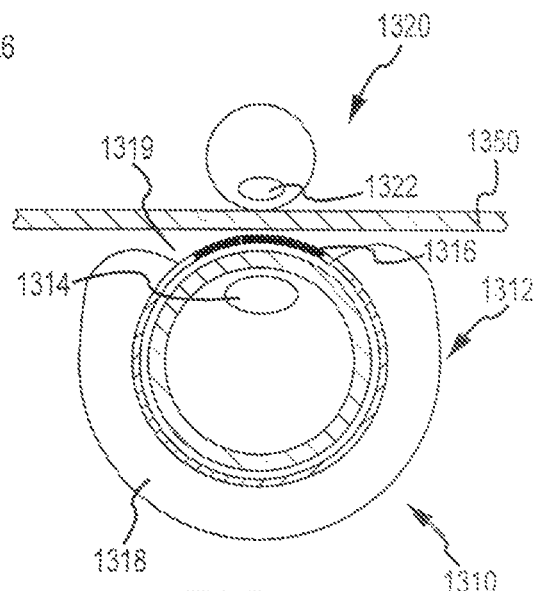
FIG. 13 illustrates aspects of ablation treatment systems and methods according to embodiments of the present invention.

As depicted in FIG. 13, a magnetic ablation structure 1310 can be designed to be used in conjunction with a magnetic positioning or guidance system 1320 placed on the epicardium of the left atrium wall 1350. When the distal portion of the endocardial ablation catheter 1312 of ablation structure 1310 is manipulated to be in proximity to the epicardial magnetic positioning or guidance system 1320, the force between attraction elements 1322 and 1314 can cause the catheter 1312 to rotate or self-position, thus orienting or placing the attraction element or magnet 1314 and the ablation element or electrode 1316 as close as possible to the epicardial surface. In other words, the ablation electrode 1316 can automatically orient itself to be contacting or positioned very near the endocardium. In that position, the balloon structure 1318 can isolate the ablation element 1316 from the blood contained within the left atrium. In some embodiments, saline can be slowly infused at the ablation electrode site to gradually force out residual blood from the ablation zone 1319. The balloon 1318 can also serve to electrically and thermally isolate the ablation element 1316 from the blood flowing in the atria, which has at least two benefits: the applied energy is directed only into the target cardiac tissue, and the lack of conductive heat loss into the blood stream enables better temperature-feedback control of the applied lesion-making energy. The fluid used to inflate the balloon 1318 could include a gas that is readily absorbed into blood ($CO_2$ or $N_2O$) or the fluid could be saline. Such gases can provide beneficial thermal isolation properties. Saline can provide beneficial neutral buoyancy properties.

FIG. 14A illustrates an exemplary electrode catheter for use in accordance with embodiments of the present invention. As shown here, the electrode catheter includes a catheter assembly 1440 having several proximal leads 1442, a handle 1444 including a steering mechanism, and a catheter 1446. The handle 1444 includes a steering device which, in turn, can include a mechanism having a screw for tension adjustment and a guide wire which extends into the catheter 1446. The catheter 1446 terminates at its distal end in a tip 1448. As depicted in FIG. 14B, distal tip 1448 can include an electrode 1450, several electrode rings 1452, a control wire assembly 1454 which is operably connected to the steering device of handle 1440, a thermistor (not shown) and a distal tube covering 1456. The thermistor can be used to determine the temperature at the electrode tip 1450 to assist with RF application. The distal tip 1448 can include four, six or eight electrode rings 1452 which are used for mapping. In the distal tip 1448, the electrode 1450 can be formed of a magnetic material as described elsewhere herein. The distal tube cover 1456 can be formed of a material such as polyurethane. The electrode rings 1452 may be formed of any conventional electrode material, for example platinum. The outer diameter of the distal tip 1440 can be varied as appropriate, for example about 6 to 8 French (F), or optionally about 7 F.

Figure 14C:
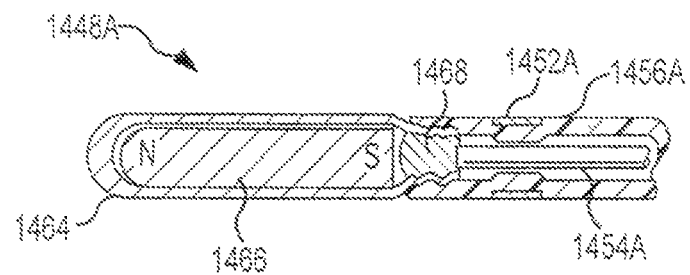
Figure 14D:
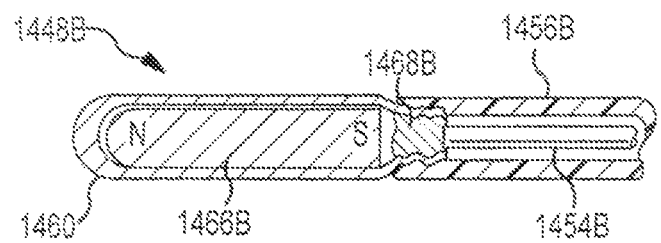

Another example of an ablation catheter 1448A is depicted in FIG. 14C. The catheter contains a control wire assembly 1454A, a distal tube covering 1456A, and electrode rings 1452A equivalent to those of the example in FIG. 14B. The catheter further contains an ablation tip 1464 which may for example be formed of a platinum iridium alloy, which, in conjunction with the electrode rings 1452A supplies the ablation function. The ablation tip 1464 surrounds a permanent magnetic core 1466. A soldered joint 1468 fastens the tip 1464 to the control wire assembly 1454A. FIG. 14D depicts a catheter 1448B that can function as an anchoring catheter, with a magnetic tip but for example without mapping or ablation functions (i.e., used in procedures involving unipolar ablation). The catheter body 1456B, the control wire assembly 1454B and the magnetic core 1466B may be equivalent or similar to embodiments described elsewhere herein. The distal tip covering 1460 over the magnetic core 1466B can be formed of a biocompatible material which does not interfere with the magnetic properties of the core 1466. Examples of such biocompatible materials include gold, platinum, platinum alloys, and plastics such as polyurethane or Teflon. A solder or pressure-fit joint 1468B can fasten the distal tip to the catheter body 1456B by appropriate means such as soldering.

Embodiments of the present invention encompass systems and methods that involve the use of an attraction element and an electrode disposed on an ablation or guiding assembly. For example, a distal structure of a catheter may include an internal magnet, surrounded at least partially by a metal electrode. The metal electrode may include a nonmagnetic or nonmagnetizable material, such as platinum. For example, the metal electrode may include a material that does not change structure in the presence of a magnetic field, or that does not create or generate a magnetic field. In some embodiments, a system may include an interior assembly for use near the endocardium, and an exterior assembly for use near the epicardium. In some embodiments, an attraction element, optionally with an ablation element, is included on an interior endocardial assembly, and an ablation element, optionally with and attraction element, is included on an exterior epicardial assembly. In some embodiments, an ablation element, optionally with an attraction element, is included on an interior endocardial assembly, and an attraction element, optionally with an ablation element, is included on an exterior epicardial assembly.

Embodiments of the present invention may utilize systems and methods for controlling tissue ablation using temperature sensing elements, for example such as those described in U.S. Pat. No. 5,769,847, the content of which is incorporated herein by reference.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method of forming a lesion on an endocardial tissue of a patient's heart, comprising:
   placing an ablation assembly inside of the heart and adjacent to the endocardial tissue, the ablation assembly comprising an ablation element, a support structure, and a first attraction element;
   expanding the support structure;
   placing a guiding assembly out side of the heart, the guiding assembly comprising a second attraction element, wherein a magnetic attraction between the first and second attraction elements draws the expanded support structure toward the endocardial tissue to form a space between the ablation element and the endocardial tissue; and
   forming the lesion on the endocardial tissue of the patient's heart, with the ablation element of the ablation assembly while the expanded support structure isolates the ablation element from blood flowing in the patient's heart.

2. The method according to claim 1, wherein the first attraction element comprises a magnetized element.

3. The method according to claim 1, wherein the second attraction element comprises a magnetized element.

4. The method according to claim 1, further comprising moving the second attraction element of the guiding assembly relative to the patient's heart, so as to effect a corresponding movement of the ablation element of the ablation assembly.

5. The method according to claim 1, wherein the ablation element comprises a member selected from the group consisting of a radiofreqnency ablation element, an infrared laser ablation element, a high intensity focused ultrasound ablation element, a microwave ablation element, a cryoablation ablation element, a chemical agent ablation element, a biological agent ablation element, and a radiation ablation element.

6. The method according to claim 1, wherein the ablation element comprises a member selected from the group consisting of a monopolar electrode and a bipolar electrode.

7. The method according to claim 1, wherein the guiding assembly comprises an elongate wand, and the second attraction element is coupled with a distal portion of the elongate wand.

8. The method according to claim 1, wherein the ablation assembly comprises an elongate catheter, and the first attraction element is coupled with a distal portion of the elongate catheter.

9. The method according to claim 1, wherein the ablation element is coupled with the distal portion of the elongate catheter.

10. A system for forming a lesion on an endocardial tissue of the patient's heart, comprising:
    an ablation assembly comprising an ablation element, a catheter body, a support structure having a section that does not extend circumferentially about the catheter body, and a first attraction element; and
    guiding assembly comprising a second attraction element, wherein the ablation element is disposed between the first attraction element and the section of the support structure that does not extend circumferentially about the catheter body, and
    wherein a magnetic attraction is present between the first and second attraction elements.

11. The system according, to claim 10, wherein the first attraction element comprises a magnetized element.

12. The system according to claim 10, wherein the second attraction element comprises a magnetized element.

13. The system according to claim 10, wherein the ablation element comprises a member selected from the group consisting of a radiofrequency ablation element, an infrared laser ablation element, a high intensity focused ultrasound ablation element, a microwave ablation element, a cryoablation ablation element, a chemical agent ablation element, a biological agent ablation element, and a radiation ablation element.

14. The system according to claim 10, wherein the ablation element comprises a member selected from the group consisting of a monopolar electrode and a bipolar electrode.

15. The system according to claim 10, wherein the guiding assembly comprises an elongate wand, and the second attraction element is coupled with a distal portion of the elongate wand.

16. The system according to claim 10, wherein the ablation assembly comprises an elongate catheter, and the first attraction element is coupled with a distal portion of the elongate catheter.

17. The system according to claim 16, wherein the ablation element is coupled with the distal portion of the elongate catheter.

18. A method of forming a lesion on an endocardial tissue of a patient's heart, comprising:
    placing an ablation assembly inside of the heart and adjacent to the endocardial tissue, wherein the ablation assembly comprises an elongate catheter having a distal portion, an ablation element coupled with the distal portion, a first attraction element coupled with the distal portion, and a balloon coupled with the distal portion;
    placing a guiding assembly outside of the heart, wherein the guiding assembly comprises an elongate wand having a distal portion, and a second attraction element coupled with the distal portion of the elongate wand;
    positioning the ablation assembly and the guiding assembly such that a magnetic attraction is present between the first and second attraction elements;
    inflating the balloon to provide a cavity between the ablation element and a surface of the endocardial tissue; and
    forming the lesion on the endocardial tissue of the patient's heart with the ablation element of the ablation assembly.

19. The method according to claim 18, wherein the ablation element comprises an electrode ring.

20. The method according to claim 18, wherein the inflated balloon extends circumferentially about the elongate catheter at a first localion distal to the ablation element, and at a second location proximal to the ablation element.

* * * * *

UNITED STATES PATENT AND TRADEMARK OFFICE
CERTIFICATE OF CORRECTION

| | | |
|---|---|---|
| PATENT NO. | : 8,430,875 B2 | Page 1 of 1 |
| APPLICATION NO. | : 12/781072 | |
| DATED | : April 30, 2013 | |
| INVENTOR(S) | : Tamer Ibrahim et al. | |

It is certified that error appears in the above-identified patent and that said Letters Patent is hereby corrected as shown below:

In the Claims:

Column 25, line 12, please delete "out side" and insert --outside--.

Column 25, line 34, please delete "radiofreqnency" and insert --radiofrequency--.

Column 26, line 56, please delete "localion" and insert --location--.

Signed and Sealed this
Thirteenth Day of August, 2013

Teresa Stanek Rea
*Acting Director of the United States Patent and Trademark Office*